(12) United States Patent
Harttig et al.

(10) Patent No.: US 11,253,177 B2
(45) Date of Patent: Feb. 22, 2022

(54) SENSOR ASSEMBLY FOR DETECTING AT LEAST ONE ANALYTE IN A BODY FLUID

(71) Applicant: ROCHE DIABETES CARE, INC., Indianapolis, IN (US)

(72) Inventors: Herbert Harttig, Neustadt (DE); Oliver Kube, Worms (DE); Michael Orth, Grossniedesheim (DE); Helmut Walter, Heppenheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 749 days.

(21) Appl. No.: 15/982,474

(22) Filed: May 17, 2018

(65) Prior Publication Data
US 2018/0263543 A1   Sep. 20, 2018

Related U.S. Application Data

(63) Continuation of application No. PCT/EP2016/078223, filed on Nov. 21, 2016.

(30) Foreign Application Priority Data

Nov. 19, 2015 (EP) .................................... 15195366

(51) Int. Cl.
*A61B 5/145* (2006.01)
*A61B 5/1486* (2006.01)

(52) U.S. Cl.
CPC ...... *A61B 5/14865* (2013.01); *A61B 5/14532* (2013.01); *A61B 2560/045* (2013.01); *A61B 2560/063* (2013.01)

(58) Field of Classification Search
CPC ............ A61B 5/14865; A61B 5/14532; A61B 2560/045; A61B 2560/063; A61B 5/00
See application file for complete search history.

(56) References Cited

U.S. PATENT DOCUMENTS

| | | |
|---|---|---|
| 5,413,690 A | 5/1995 | Kost et al. |
| 5,762,770 A | 6/1998 | Pritchard et al. |

(Continued)

FOREIGN PATENT DOCUMENTS

| | | |
|---|---|---|
| DE | 954 712 C | 12/1956 |
| DE | 200 20 566 U1 | 1/2002 |

(Continued)

OTHER PUBLICATIONS

International Search Report and Written Opinion of the International Searching Authority; PCT/EP2016/078223; dated Feb. 21, 2017; 8 pages.

(Continued)

*Primary Examiner* — Jacqueline Cheng
*Assistant Examiner* — Tho Q Tran
(74) *Attorney, Agent, or Firm* — Bose McKinney & Evans LLP

(57) ABSTRACT

A sensor assembly for detecting at least one analyte in a body fluid includes an electrochemical sensor, a body mount that attaches to a body of a user and an inserter that transfers the sensor to the body mount. A first adhesive is attached to one or both of the body mount or the sensor, and the first adhesive attaches the sensor to the body mount. A second adhesive is attached to one or both of the sensor or the inserter and releasably attaches the sensor to the inserter. The assembly has an initial position in which the sensor is attached to the inserter via the second adhesive and a final position in which the sensor is attached to the body mount via the first adhesive. Transferring the sensor from the initial position to the final position releases the sensor from the inserter.

21 Claims, 11 Drawing Sheets

(56) References Cited

U.S. PATENT DOCUMENTS

| | | |
|---|---|---|
| 5,798,031 A | 8/1998 | Charlton et al. |
| 6,129,823 A | 10/2000 | Hughes et al. |
| 6,360,888 B1 | 3/2002 | McIvor et al. |
| 2005/0013731 A1 | 1/2005 | Burke et al. |
| 2006/0016700 A1* | 1/2006 | Brister ................. A61B 5/6848 205/777.5 |
| 2006/0020186 A1 | 1/2006 | Brister et al. |
| 2007/0073129 A1 | 3/2007 | Shah et al. |
| 2007/0163880 A1 | 7/2007 | Woo et al. |
| 2008/0058678 A1 | 3/2008 | Miyata et al. |
| 2008/0242962 A1 | 10/2008 | Roesicke et al. |
| 2008/0249383 A1* | 10/2008 | Sass ................... A61B 5/14532 600/345 |
| 2010/0113897 A1* | 5/2010 | Brenneman .......... A61B 5/6833 600/310 |
| 2011/0191044 A1* | 8/2011 | Stafford ................. A61B 5/742 702/65 |
| 2011/0230743 A1* | 9/2011 | Inciardi .............. A61B 5/14532 600/365 |
| 2012/0244043 A1 | 9/2012 | Leblanc et al. |
| 2013/0189720 A1* | 7/2013 | Petisce ................. G01N 27/327 435/25 |
| 2013/0338598 A1* | 12/2013 | Gyrn ................... A61M 5/1723 604/174 |
| 2015/0025345 A1 | 1/2015 | Funderburk et al. |
| 2015/0087942 A1 | 3/2015 | Brauker et al. |
| 2016/0331284 A1* | 11/2016 | Pace ................... A61B 5/14532 |
| 2017/0087270 A1* | 3/2017 | Wibaux ................ C09J 133/08 |

FOREIGN PATENT DOCUMENTS

| | | |
|---|---|---|
| RU | 2 442 986 C2 | 2/2012 |
| WO | WO 2007/071562 A1 | 6/2007 |
| WO | WO 2010/040448 A1 | 4/2010 |
| WO | WO 2011/041531 A1 | 4/2011 |
| WO | WO 2013/066854 A1 | 5/2013 |

OTHER PUBLICATIONS

Extended European Search Report; EP 15195366.8; dated May 17, 2016; 6 pages.

* cited by examiner

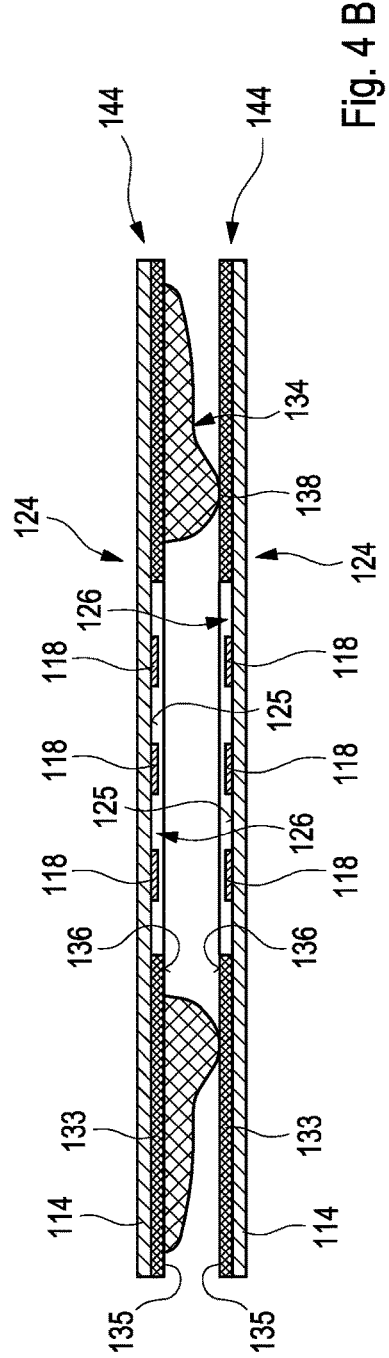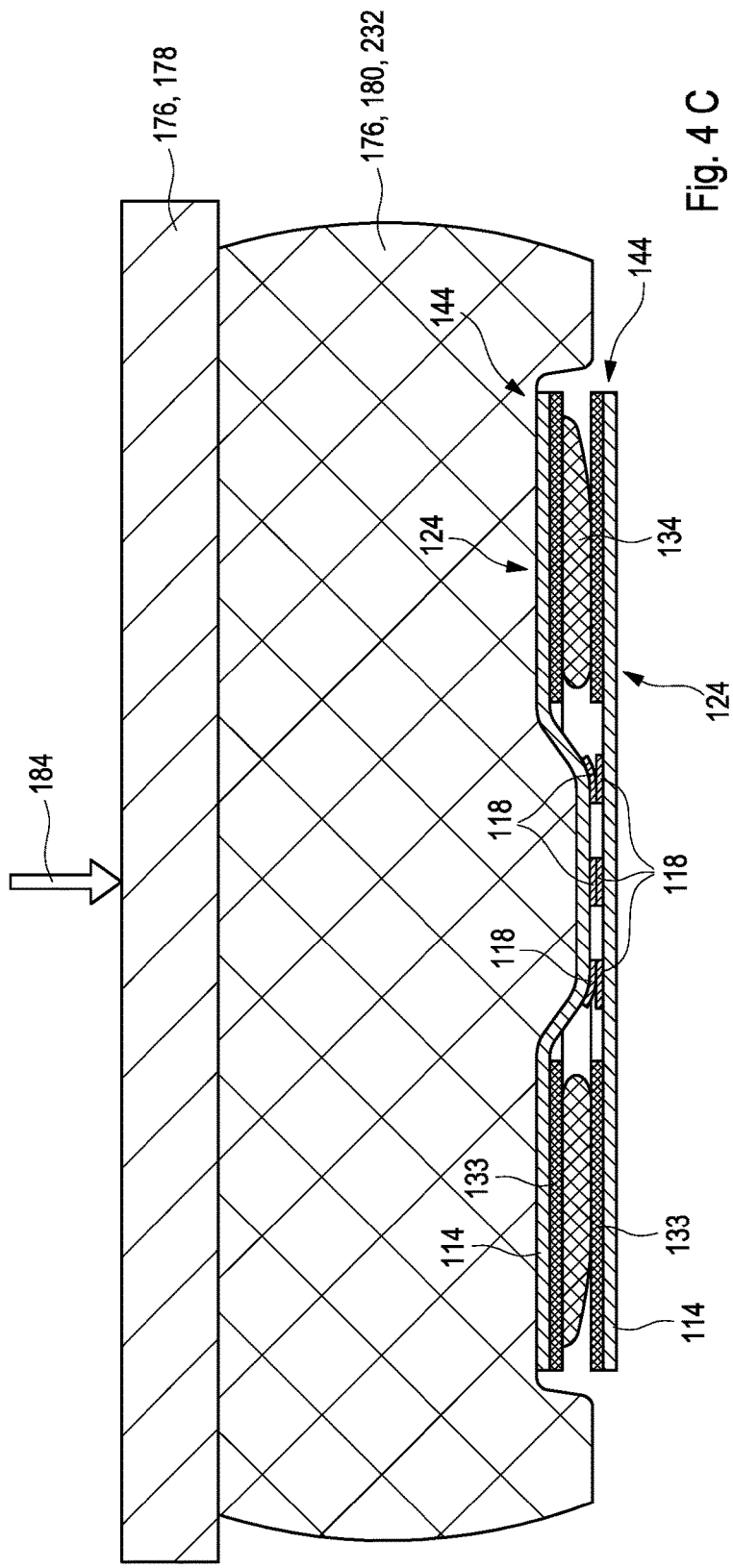

SENSOR ASSEMBLY FOR DETECTING AT LEAST ONE ANALYTE IN A BODY FLUID

RELATED APPLICATIONS

This application is a continuation of PCT/EP2016/078223, filed Nov. 21, 2016, which claims priority to EP 15195366.8, filed Nov. 19, 2015, the entire disclosures of both of which are hereby incorporated by reference.

BACKGROUND

This disclosure relates to a sensor assembly for detecting at least one analyte in a body fluid and a method for mounting a sensor for detecting at least one analyte in a body fluid to a body mount attachable to a body of a user. The devices and methods according to this disclosure may mainly be used for long-term monitoring of an analyte concentration in a body fluid, such as for long-term monitoring of a blood glucose level or of the concentration of one or more other types of analytes in a body fluid. This disclosure may both be applied in the field of home care as well as in the field of professional care, such as in hospitals. Other applications are feasible.

Monitoring certain body functions, more particularly monitoring one or more concentrations of certain analytes, plays an important role in the prevention and treatment of various diseases. Without restricting further possible applications, the following text reference is made to blood-glucose monitoring. However, additionally or alternatively, this disclosure can also be applied to other types of analytes.

Blood glucose monitoring, besides by using optical measurements, specifically may be performed by using electrochemical bio sensors. Examples of electrochemical biosensors for measuring glucose, specifically in blood or other body fluids, are known from U.S. Pat. Nos. 5,413,690 A, 5,762,770 A, 5,798,031 A, 6,129,823 A or US 2005/0013731 A1.

In addition to so-called spot measurements, in which a sample of a bodily fluid is taken from a user in a targeted fashion and examined with respect to the analyte concentration, continuous measurements are increasingly becoming established. Thus, in the recent past, continuous measuring of glucose in the interstitial tissue (also referred to as continuous monitoring, CM) for example has been established as another important method for managing, monitoring and controlling a diabetes state.

In the process, the active sensor region is applied directly to the measurement site, which is generally arranged in the interstitial tissue, and, for example, converts glucose into electrical charge by using an enzyme (e.g., glucose oxidase, GOD), which charge is related to the glucose concentration and can be used as a measurement variable. Examples of such transcutaneous measurement systems are described in U.S. Pat. No. 6,360,888 B1 or in US 2008/0242962 A1.

Hence, current continuous monitoring systems typically are transcutaneous systems or subcutaneous systems, wherein both expressions, in the following, will be used equivalently. This means that the actual sensor or at least a measuring portion of the sensor is arranged under the skin of the user. However, an evaluation and control part of the system (also referred to as a patch) is generally situated outside of the body of the user, outside of the human or animal body. In the process, the sensor is generally applied using an insertion instrument, which is likewise described in U.S. Pat. No. 6,360,888 B1 in an exemplary fashion. Other types of insertion instruments are also known.

The sensor typically comprises a substrate, such as a flat substrate, onto which an electrically conductive pattern of electrodes, conductive traces and contact pads may be applied. In use, the conductive traces typically are isolated by using one or more electrically insulating materials. The electrically insulating material typically further also acts as a protection against humidity and other detrimental substances and, as an example, may comprise one or more cover layers such as resists.

As outlined above, in transcutaneous systems, a control part is typically required, which may be located outside the body tissue and which has to be in communication with the sensor. Typically, this communication is established by providing at least one electrical contact between the sensor and the control part, which may be a permanent electrical contact or a releasable electrical contact. Examples of electrical contacts for contacting a triangular assembly of contact pads are shown, e.g., in DE 954712 B. Other techniques or providing electrical contacts, such as by appropriate spring contacts, are generally known and may be applied.

In order to avoid detrimental effects of the aggressive environment onto the conductive properties of the electrical contact, the region of the electrical contact is typically encapsulated and protected against humidity. Generally, encapsulations of electrical locks and contacts by using appropriate seals is known from, e.g., DE 200 20 566 U1. Specifically in transcutaneous or subcutaneous sensors, in which the region of electrical contact between the sensor and the control part is close to the human skin, an efficient protection against humidity, dirt, sweat and detergents, such as detergents used for body care, is crucial.

US 2008/0242962 A1 discloses a system for in-vivo measurement of analyte concentrations. A sensor is part of a replaceable sensor carrier unit that comprises a sealed housing in which the sensor is disposed. A sealed housing of the sensor carrier unit protects the sensitive sensor from adverse environmental influences. Additionally, the housing of the sensor carrier unit locks to a base station in order to couple the sensor to a base station. The sensor can be exposed for insertion after coupling, for example by means of a predetermined breaking point for the sensor that is provided on the housing of the sensor carrier unit.

WO 2011/041531 A1 discloses systems and methods for providing a compressible interconnect for allowing electrical communication between an electronics unit and an analyte sensor in an on-body analyte monitoring device and for reducing the Z-height of an on-body analyte monitoring device by utilizing interconnects. Therein, the electronics unit comprises a seal disposed proximate an elongated interconnect. The seal is an individually molded component made of low duromer silicone, rubber or some other material TPE. In some embodiments, the interconnect extends approximately 1 mm beyond the face of the seal. When the electronics unit is locked into position, the interconnect compresses and makes contact with the conductive pads on the sensor. The seal also compresses to form a barrier around the perimeter of the interconnect/sensor connection. The interconnect may work without the seal, however once liquid or dust got in, the interconnect/sensor interface may be compromised and fail.

US 2015/0087942 A1 relates to systems and methods for transcutaneous measurement of glucose in a host. The device for measuring an analyte in a host comprises a sensor operably connected to sensor electronics, the sensor electronics configured for measuring an analyte in a host. At least one electrical contact is configured to connect the sensor to the sensor electronics and a sealing member at least partially surrounds the sensor and the electrical contact. Additionally an adhesive pad is placed over some or all of the sensor system such that after sensor insertion is complete adhesion is ensured and optionally to ensure an airtight seal or watertight seal around the wound exit-site (or sensor insertion site). The sealing member comprises a material selected from the group consisting of silicone, silicone/polyurethane hybrid, polyurethane, polysulfide, and mixtures thereof. The sealing member further comprises a sealant sandwiched between an upper portion of the sealing member and a lower portion of the sealing member.

In other fields of technology, such as the technical field of microfluidic devices, sealing may also be an issue, such as sealing against leaking of liquids. As an example, US 2012/0244043 A1 relates to gaskets for sealing fluid interfaces in micro fluidic systems. In particular, a microfluidic device includes at least one internal channel, and at least one port in fluid communication with the channel. A seal is associated with the port and is configured to receive a fluid transport mechanism. The seal can be formed from an elastomeric material that is compatible for use with fluorinated oil and resists flaking and degradation. In particular embodiments, the gasket is made of a thermoplastic silicone elastomer, such as Geniomer® 200 Silicone TPE (Wacker Chemie), which is a two phase block copolymer made up of a soft polydimethylsiloxane (PDMS) phase and a hard aliphatic polyisocyanate phase. Such materials are capable of resisting flaking and degradation in the presence of a fluorinated oil, and/or after sealingly receiving a means for introducing a sample fluid (e.g., a tubing or pipette).

A major challenge in the field of continuous monitoring further resides in appropriate techniques for connecting the sensor to the control part and/or a body mount being a part of the control part. The connection typically takes place during or simultaneously to an insertion of the sensor into the body tissue, even though the electrical/mechanical connection of these components and the insertion, in their nature, are two distinct processes. Typically, in the art of electronics, for interconnecting to electrical components, appropriate electrical connectors such as male/female plugs are used, which often also include a self-centering or self-alignment mechanism. Further, flat plugs are generally known which may be inserted into a flat jack. In order to increase stability and durability of the electrical interconnections, at least one of the contact partners may provide a clip or spring element for maintaining a mechanical connection.

US 2015/025345 A1 discloses a single-use sensor inserter and a single-use adhesive mount removably attached to the bottom thereof. As an overview of the operation of inserter kit, the kit comes packaged generally with a sensor pre-loaded within inserter and with inserter in a "cocked" state. On insertion the sensor is pulled from introducer sharp and held in place by the sensor contact portion on top of adhesive tape adhering to orthogonal surface of sensor. The geometries of the sensor dimple and mating introducer dimple are chosen to create a separation force between them that is less than the adhesion force of the tape on orthogonal surface, but great enough to retain sensor in introducer sharp during typical shipping and product handling shock loads. Driving surface beneath the shuttle presses down on top of orthogonal surface to ensure good contact with adhesive tape before the shuttle retracts with the introducer sharp.

WO 2010/040448 A1 discloses an insertion device comprising an insertion needle holder, a drive mechanism for linearly moving the insertion needle holder in a puncturing direction, and at least one actuating element for actuating a drive mechanism. Here the drive mechanism converts a driving motion of the actuating element, which extends transversely or opposite to the puncturing direction, into a puncturing motion of the insertion needle holder. The sensor transfer is accomplished via locking element on the body mount and the inserter.

US 2007/163880 A1 discloses a transcutaneous analyte sensor system including an applicator, a mounting unit, and an electronics unit. The mounting unit includes a base adapted for mounting on the skin of a host, a sensor adapted for trans-dermal insertion through the skin of a host and one or more contacts configured to provide secure electrical contact between the sensor and the electronics unit. An applicator is provided for inserting the sensor through the host's skin at the appropriate insertion angle with the aid of a needle and for subsequent removal of the needle using a continuous push-pull action. The applicator comprises an applicator body that guides the applicator components and includes an applicator body base configured to mate with the mounting unit during insertion of the sensor into the host. The mate between the applicator body base and the mounting unit can use any known mating configuration, for example, a snap-fit, a press-fit, an interference-fit, or the like, to discourage separation during use. One or more release latches enable release of the applicator body base, for example, when the applicator body base is snap fit into the mounting unit.

Despite the advantages and the progress achieved by the above-mentioned developments, specifically in the field of continuous monitoring technology, some significant technical challenges remain. Thus, generally, known techniques for protecting and electrical contact between a sensor and a control part generally are rather complex. An assembly of a plurality of components is generally required, which typically implies a complex and costly manufacturing process. Further, known techniques generally require voluminous components, which is an issue, specifically considering the fact that miniaturizing the sensor systems is a factor contributing to the convenience of use. Specifically in case complex encapsulation parts manufactured by plastic molding techniques are required for protecting the electrical contacts, a rising of costs and sensor volume typically has to be taken into account. Further, cleaning of complex protective covers, such as protections including O-rings or other seals, turns out to be difficult. Still further, specifically when following the goal of miniaturization, the precision of available sealing elements such as O-rings is challenging, which typically necessitates costly selection processes.

Further, when using sealing elements such as O-rings, for protecting the electrical contacts, besides the additional volume required for holding these elements, the precise guiding of the contacting components is challenging and requires additional space. Further, O-rings typically create an additional friction which has to be overcome when interconnecting the components. Generally, when using conventional electrical connectors such as jacks and/or plugs or other types of male/female connectors, additional effort is required, since the connecting of these plug connectors typically requires an insertion force which increases the needs for rigidity and sustainability of the connectors and, thus, the needs for space.

This disclosure teaches a sensor assembly for detecting at least one analyte in a body fluid and a method for mounting a sensor for detecting at least one analyte in a body fluid to a body mount attachable to a body of a user, which at least partially avoid the shortcomings of known devices and methods of this kind and which at least partially address the above-mentioned challenges. Specifically, devices and methods are disclosed which avoid complex and voluminous interconnectors, which may be implemented in large-scale production processes and which are easy to use and cost-efficient.

A sensor assembly for detecting at least one analyte in a body fluid and a method of mounting a sensor for detecting at least one analyte in a body fluid to a body mount attachable to a body of a user are recited in the independent claims. Preferred embodiments, which might be realized in an isolated fashion or in any arbitrary combination are recited in the dependent claims.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

With particular regard to the appended claims, it shall be understood that a given feature or element is to be interpreted as "at least one" or "one or more" unless a singular interpretation is made explicit herein. By way of example, a claim reciting "B" should be interpreted as "one or more B" or "at least one B."

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. This disclosure may, as the skilled person will recognize, be performed by using alternative features Similarly, features introduced by "in an embodiment of this disclosure" or similar expressions are intended to be optional features, without any restriction regarding alternative embodiments of this disclosure, without any restrictions regarding the scope of this disclosure and without any restriction regarding the possibility of combining the features introduced in such way with other optional or non-optional features of this disclosure.

In a first aspect of this disclosure, a sensor assembly for detecting at least one analyte in a body fluid is disclosed. The sensor assembly comprises at least one sensor, wherein the sensor is an electrochemical sensor. Further, the sensor assembly comprises at least one body mount configured for attachment to a body of a user and at least one insertion element for transferring the sensor to the body mount. Further, the sensor assembly comprises at least one first adhesive element attached to one or both of the body mount or the sensor and at least one second adhesive element attached to one or both of the sensor or the insertion element. The first adhesive element is configured for attaching the sensor to the body mount. The second adhesive element is configured for releasably attaching the sensor to the insertion element. The insertion element is configured to transfer the sensor from an initial position, in which the sensor is attached to the insertion element via the second adhesive element, into a final position in which the sensor is attached to the body mount via the first adhesive element and released from the insertion element.

The term "sensor assembly" generally refers to a group of at least two elements or components which are capable of interacting in order to perform at least one sensor function, in the present case in order to perform at least one detection of the at least one analyte in the body fluid and/or in order to contribute to the at least one detection of the at least one analyte in the body fluid. The sensor assembly generally may also be referred to as a sensor system, a sensor kit or a sensor device.

The sensor assembly may particularly be a transcutaneous sensor system wherein the sensor is wholly or at least partly arranged within a body tissue of a patient or a user. At least one component of the sensor system may be wholly or partly outside of the body tissue, for example the control part. The sensor may be interconnected through a tissue surface or skin of the patient or the user. Thus, the sensor may partially be inserted into the body tissue, such as with a sensor portion of the sensor, and partially may be located outside the body tissue, such as with a connector portion of the sensor. Still, other embodiments are feasible.

As generally used within this disclosure, the terms "patient" and "user" may refer to a human being or an animal, independent from the fact that the human being or animal, respectively, may be in a healthy condition or may suffer from one or more diseases. As an example, the patient or the user may be a human being or an animal suffering from diabetes. However, additionally or alternatively, this disclosure may be applied to other types of users or patients.

As further used herein, the term "body fluid" generally may refer to a fluid which typically is present in a body or body tissue of the user or the patient and/or which may be produced by the body of the user or the patient. As an example for body tissue, interstitial tissue may be named. Thus, as an example, the body fluid may be selected from the group consisting of blood and interstitial fluid. However, additionally or alternatively, one or more other types of body fluids may be used, such as saliva, tear fluid, urine or other body fluids. During detection of the at least one analyte, the body fluid may be present within the body or body tissue. Thus, specifically, as will be outlined in further detail below, the sensor may be configured for detecting at least one analyte in a body tissue.

As further used herein, the term "analyte" may refer to an arbitrary element, component or compound which may be present in the body fluid and the presence and/or the concentration of which may be of interest for the user, the patient or medical staff such as a medical doctor. Particularly, the analyte may be or may comprise an arbitrary chemical substance or chemical compound which may take part in the metabolism of the user or the patient, such as at least one metabolite. As an example, the at least one analyte may be selected from the group consisting of glucose, cholesterol, triglycerides, lactate. Additionally or alternatively, however, other types of analytes may be used and/or any combination of analytes may be determined. The detection of the at least one analyte specifically may be an analyte-specific detection.

As further used herein, the term "detect" generally refers to the process of determining the presence and/or the quantity and/or the concentration of the at least one analyte. Thus, the detection may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one signal specifically may be or may comprise at least one electronic signal such as at least one voltage and/or at least one current. The at least one signal may be or may comprise at least one analogue signal and/or may be or may comprise at least one digital signal.

As further used herein, the term "determining a concentration" generally may refer to a process of generating at least one representative result or a plurality of representative results indicating the concentration of the analyte in the body fluid.

As further used herein, the term "sensor" may generally refer to an arbitrary element which is adapted to perform the above-mentioned process of the detection and/or which is adapted to be used in the above-mentioned process of the detection. Thus, the sensor specifically may be adapted to determine the concentration of the analyte and/or a presence of the analyte.

The sensor may particularly be a "transcutaneous sensor." As used herein, the term transcutaneous sensor generally refers to a sensor which is adapted to be fully or at least partly arranged within a body tissue of the patient or the user. For this purpose, the sensor generally may be dimensioned such that a transcutaneous insertion is feasible, such as by providing a width in a direction perpendicular to an insertion direction of no more than 5 mm, preferably of no more than 2 mm, more preferably of no more than 1.5 mm. The sensor may have a length of less than 50 mm, such as a length of 30 mm or less, e.g., a length of 5 mm to 30 mm. It shall be noted, however, that other dimensions are feasible. In order to further render the sensor to be usable as a transcutaneous sensor, the sensor may fully or partially provide a biocompatible surface, i.e., a surface which, at least during durations of use, do not have any detrimental effects on the user, the patient or the body tissue. As an example, the transcutaneous sensor may fully or partially be covered with at least one biocompatible membrane, such as at least one polymer membrane or gel membrane which is permeable for the at least one analyte and/or the at least one body fluid and which, on the other hand, retains sensor substances such as one or more test chemicals within the sensor and prevents a migration of these substances into the body tissue.

The sensor may comprise at least one substrate. The sensor may further have at least two electrodes applied to the substrate, wherein the electrodes are adapted for detecting the analyte. The sensor may further have at least two contact pads applied to the substrate and at least two electrical traces applied to the substrate. The electrical traces may electrically connect the electrodes and the contact pads. The substrate may comprise one or more components, which fully or partially may cover one or more of the electrodes, the conductive traces or the contact pads. Thus, generally, the substrate may comprise a multilayer setup, wherein the electrodes, conductive traces and contact pads not necessarily have to be on an outer surface of the multilayer setup. Generally, however, the electrodes preferably may be fully or partially left open and uncovered or covered by one or more permeable materials, only. Similarly, the contact pads may be left open or may be covered by one or more electrically conductive materials, only. Thus, as an example, the conductive traces typically may be isolated by using one or more electrically insulating materials, such as one or more electrically insulating cover layers, which, as a definition, may form part of the substrate. Consequently, the sensor may further comprise at least one electrically insulating material, which may form part of the substrate, and which may fully or partially cover the conductive traces and which may at least partially leave open or leave free the electrodes and the contact pads. The electrically insulating material typically further also acts as a protection against humidity and other detrimental substances and, as an example, may comprise one or more cover layers such as resists.

The sensor may further comprise a sealing ring fixedly applied to the substrate. In case the substrate comprises a plurality of components such as a multilayer setup, the sealing ring may be applied to one or more of the components. Thus, as an example, the substrate may comprise at least one base layer, such as at least one insulating base layer, to which one or more of the electrodes, the conductive traces and all the contact pads may be applied. As outlined above, the substrate may further comprise at least one insulating material which fully or partially covers one or more of the electrodes, the conductive traces or the contact pads. As an example, the at least one insulating material may at least partially leave open the electrodes and the contact pads. The insulating material, as an example, may comprise one or more insulating layers fully or partially covering one or more of the electrodes, the conductive traces of the contact pads, such as one or more insulating layers at least partially leaving open the electrodes and the contact pads. The sealing ring, as an example, may either be directly applied to the at least one insulating base layer of the substrate, such as to at least one insulating foil forming the base layer of the substrate, or to the at least one insulating material, such as the at least one insulating cover layer which fully or partially covers one or more of the electrodes, the conductive traces of the contact pads and which at least partially may leave open the electrodes and the contact pads. The sealing ring may surround the contact pads.

As described above, the sensor is an "electrochemical sensor." As used herein, an electrochemical sensor generally is a sensor which is configured to conduct an electrochemical measurement in order to detect the at least one analyte contained in the body fluid. The term "electrochemical measurement" refers to a detection of an electrochemically detectable property of the analyte, such as an electrochemical detection reaction. Thus, for example, the electrochemical detection reaction may be detected by comparing one or more electrode potentials, as further discussed below. The electrochemical sensor specifically may be adapted to and/or may be usable to generate at least one electrical sensor signal which directly or indirectly indicates the presence and/or the extent of the electrochemical detection reaction, such as at least one current and/or at least one voltage. For this purpose, as will be outlined in further detail below, the at least one electrochemical sensor provides two or more electrodes, which also are referred to as a sensor electrodes. The detection may be analyte-specific. The measurement may be a qualitative and/or a quantitative measurement. Still, other embodiments are feasible.

As further used herein, the term "electrode" may generally refer to an arbitrary element which is configured to or which is usable to electrically or electrochemically detect the analyte. Specifically, each electrode may comprise at least one conductive pad or conductive element, such as at least one metal pad and/or at least one metal element and/or at least one pad or element made of at least one conductive inorganic or organic material such as carbon and/or a conductive polymer. The at least one conductive pad or conductive element may be uncovered and/or may be covered with at least one additional material, such as at least one sensor chemical, as will be outlined in further detail below. The at least two electrodes of the sensor may be embodied such that an electrochemical reaction may take place at one or more of the electrodes, such as one or more working electrodes. Thus, the electrodes may be embodied such that an oxidation reaction and/or reduction reaction may take place at one or more of the electrodes. The electrochemical detection reaction may be detected by comparing one or more electrode potentials, such as an electrostatic potential of a working electrode with an electrostatic potential of one or more further electrodes such as a counter electrode or a reference electrode. Generally, as an example, the two or more electrodes may be usable for one or more of an amperometric, an amperostatic, a potentiometric or a potentiostatic measurement. These types of measurements generally are known to the skilled person in the art of analyte detection, such as from WO 2007/071562 A1 and/or the prior art documents disclosed therein. For potential setups of the electrodes, electrode materials or measurement setups, reference may be made to this document. It shall be noted, however, that other setups, electrode materials or measurement setups may be used within this disclosure.

The at least two electrodes may comprise at least one working electrode. As used herein, the term "working electrode" refers to an electrode being adapted for or being usable for performing at least one electrochemical detection reaction for detecting the at least one analyte in the body fluid. The working electrode may have at least one test chemical being sensitive to the analyte to be detected. The working electrode may further comprise at least one conductive working electrode pad. The conductive working electrode pad may be in contact with the at least one test chemical. Thus, the at least one test chemical may be coated onto the at least one conductive working electrode pad. The at least one test chemical may form at least one test chemical surface which may be in contact with the at least one body fluid. As an example, the at least one test chemical surface may be an open test chemical surface or may be covered by the above-mentioned at least one membrane which is permeable to the at least one analyte to be detected and/or to the body fluid or a part thereof, such that the analyte may interact with the test chemical. For potential test chemicals and/or materials for the conductive working electrode pad, again, reference may be made to WO 2007/071562 A1 and/or the prior art documents disclosed therein. Other embodiments, however, are feasible.

The one or more "working electrode pads" specifically may be formed by at least one dot, line or grid which each can form a coherent area of an electrode material. If more than one dot, line or grid of the electrode material is superimposed, the sensor may provide more than one electrode pad. All electrode pads together may build the working electrode. The sensor may comprise the working electrode with a number of electrode pads in a range from 1 to 50, preferably from 2 to 30, preferably from 5 to 20 electrode pads.

The term "test chemical" specifically may refer to an arbitrary material or a composition of materials adapted to change at least one detectable property in the presence of at least one analyte. This property may be an electrochemically detectable property. Specifically, the at least one test chemical may be a highly selective test chemical, which only changes the property if the analyte is present in the body fluid whereas no change occurs if the analyte is not present. The degree or change of the at least one property is dependent on the concentration of the analyte in the body fluid, in order to allow a quantitative detection of the analyte. As an example, the test chemical may comprise at least one enzyme, such as glucose oxidase and/or glucose dehydrogenase.

The at least two electrodes may further comprise at least one counter electrode. As used herein, the term "counter electrode" refers to an electrode adapted for performing at least one electrochemical counter reaction and adapted for balancing a current flow required by the detection reaction at the working electrode.

Additionally or alternatively, the at least two electrodes may further comprise at least one reference electrode. The reference electrode may have a stable and well-known electrode potential. The electrode potential may preferably be highly stable. The counter electrode and the reference electrode may be one of a common electrode or two separate electrodes.

Again, for potential materials usable for the counter electrode and/or the reference electrode, reference may be made to WO 2007/071562 A1 and/or the prior art documents disclosed therein. Other embodiments, however, are feasible.

The electrodes, particularly the working electrode, the counter electrode and/or the reference electrode, may have the identical dimension, The term "dimension" refers to one or more of a width, a length, a surface area, a shape of the first and the second electrodes. A shape of the electrodes may be determined by a manufacturing process, such as a cutting and/or a printing process. The shape may be rectangular or round. Still, other embodiments are feasible, such as embodiments in which the dimensions of the working electrode and the counter/reference electrodes differ and/or embodiments in which a non-circular shape or a non-rectangular shape is used. The electrodes may be made of a non-corrosive and non-passivating material. With regard to possible electrode materials, reference may be made to the prior art documents cited above.

As further used herein, the term "substrate" may generally refer to an arbitrary element which is suitable to carry one or more other elements disposed thereon or therein. As an example, the substrate may be a flat substrate, such as a substrate having a lateral extension exceeding its thickness by at least a factor of 2, at least a factor of 5, at least a factor of 10, or even at least a factor of 20 or more. The substrate specifically may have an elongated shape, such as a strip-shape and/or a bar-shape. The substrate, as an example, may comprise a shaft, specifically a shaft having an elongate shape. For example the shaft may have a shape selected from the group consisting of a strip, a needle, a tape.

The substrate may comprise at least one contact portion. The contact portion may be connected mechanically and/or electrically to at least one control part of the sensor assembly comprising the sensor, specifically to a body mount of the control part and/or to an electronics unit of the control part. The contact portion may be widened as compared to the remaining substrate, particularly compared to the shaft. The contact portion may preferably be a rectangular contact portion. Other shapes are feasible, however. Thus, the contact portion may have a shape selected from the group consisting of: round, oval, angular. Still, other embodiments are feasible.

The substrate, as outlined above, may be an elongate substrate, with the electrodes being placed at one end of the elongate substrate and the contact pads being placed on an opposing end of the substrate. The contact pads may be located in the contact portion.

The substrate may be a flexible substrate, i.e., a substrate which may be bent or deformed by forces which usually occur during wearing and insertion into the body tissue, such as forces of 10 N or less. Specifically the substrate may be made of or may contain at least one deformable material, such as at least one plastic or malleable material and/or at least one elastic material. As an example, the substrate may be or may comprise at least one foil, such as at least one foil made of one or more of a paper material, a cardboard material, a plastic material, a metal material, a ceramic material or a glass material. As an example, the substrate may comprise at least one polyimide foil. The substrate specifically may comprise at least one electrically insulating material, such as at least one electrically insulating plastic foil.

As used herein, the term "contact pad" generally refers to an element having an open or electrically contactable surface which is electrically conductive. As an example, the contact pads may be or may comprise at least one layer of at least one electrically conductive material which directly or indirectly may be deposited onto the substrate and which provides an electrically contactable surface. In a dimension or direction parallel to a surface of the substrate, the contact pads may provide a contact surface area, such as an area having a rectangular shape, a polygonal shape or a round shape. Other shapes are possible.

The contact pads may be located in the above-mentioned contact portion of the sensor. The contact pads may be fully or at least partially made of at least one metallic material. Thus, as an example, contact pads may comprise at least one gold layer. In addition or alternatively, other types of metal layers may be applied, such as at least one of: Cu, Ni, Ag, Au, Pd, Pt. Again, additionally or alternatively, the contact pads may fully or partially be made of at least one nonmetallic electrically conductive material, such as at least one of: a conductive carbon material, such as graphite, graphene, carbon nanotubes, glassy carbon; an electrically conductive organic material, such as an electrically conductive polymer.

As further used herein, the term "electrical trace" may generally refer to an arbitrary electrically conducting element which is suited or configured to electrically connect at least two electrical elements, such as, in this case, at least one contact pad with at least one associated electrode. Thus, for each electrode, at least one contact pad may be associated and the electrode and the associated contact pads may be connected via the at least one electrical trace, thereby allowing for electrically contacting, independently, each electrode via the at least one associated contact pad. The electrical traces specifically may have a shape at least in two dimensions. The electrical trace preferably may have an elongated shape, such as a length along the substrate exceeding a width in a plane of the substrate by at least a factor of 5, such as at least a factor of 10, or even at least a factor of 100. For example, the electrical trace may comprise at least one wire or path. Furthermore, the electrical trace may comprise at least one electrically conductive material. Preferably, the electrically conductive material may comprise copper. Additionally or alternatively, one or more of the materials listed above for the contact pads may be used. Further, the electrically conductive material may be or may comprise at least one material selected from the group consisting of: an electrically conductive organic material, preferably at least one electrically conductive polymer, an electrically conductive carbon material, preferably one or more of graphite, graphene, glassy carbon and carbon nanotubes; a metal preferably from the group consisting of Cu, Ni, Ag, Au, Pd and Pt. However, additionally or alternatively, one or more other electrically conductive materials may be used.

The sensor may further comprise at least one electrically insulating material. As further used herein, the term "electrically insulating material" may generally refer to a material having an electric conductivity below 0.001 S/cm, preferably below 0.0001 S/cm, most preferably below 10-6 S/cm, even more preferably below 10-8 S/cm, below 10-9 S/cm, below 10-10 S/cm or even below 10-11 S/cm. For example the electrically insulating material may comprise an insulating resist. However, other materials are feasible. The electrically insulating material may at least partially cover the electrical traces, the insulating material leaving open the electrodes and the contact pads. The electrically insulating material may comprise at least one insulating cover layer covering the electrical traces. The electrically insulating material may form openings, wherein the electrodes are located within the openings.

The electrically insulating material may at least not fully cover the contact portion. The electrically insulating material may be distinct from the sealing ring. The sealing ring may exceed the electrically insulating material, specifically at least one insulating layer may be formed by the electrically insulating material, in height, preferably by at least a factor of 1.5, more preferably by at least a factor of 2. Thus, the at least one sealing ring specifically may protrude from the surface of the sensor and/or the sensor substrate and/or from a surface of the at least one electrically insulating material covering the sensor and/or the sensor substrate. The sealing ring may be fully or partially applied onto the electrically insulating material.

The sensor may further comprise the sealing ring fixedly applied to the substrate the sealing ring surrounding the contact pads. As further used herein, the term "sealing ring" may generally refer to an arbitrary element which is configured to surround one or more elements to be sealed off from environmental influences such as moisture. Specifically, the sealing ring may be configured to surround the at least one element to be sealed off from the environmental influences in at least two dimensions. Thus, the sealing ring may be a ring-shaped element. The ring-shaped element may have the shape of a circular ring, a polygonal ring, an oval ring or any other closed shape. The sealing ring specifically may be made of at least one compressible material.

As further used herein, the term "fixedly applied" generally refers to the fact that the sealing ring contacts the substrate and is mounted onto the substrate in such a way that the sealing ring does not come off the substrate without exerting additional forces to the sealing ring and/or the substrate in order to remove these elements from each other, such as additional forces exceeding the gravitational force. Specifically, the sealing ring may be adhered to the substrate by material engagement, such as by directly gluing the sealing ring to the substrate. Specifically, the sealing ring itself may be made of an adhesive material which directly adheres to the substrate, thereby fixedly applying the sealing ring to the substrate by adhesive forces. Thus, specifically, no additional adhesive material between the sealing ring and the substrate may be used, and the sealing ring may directly contact the substrate.

The sealing ring may surround the contact pads. As an example, the contact pads may be located on a surface of the substrate and/or of the sensor, such as in a contact portion of the substrate. The sealing ring may also be located on this surface, specifically in the contact portion of the substrate. As outlined above, therein, the sealing ring may directly contact the substrate and/or may contact at least one insulating material interposed in between the substrate and the sealing ring. The sealing ring may shield an interior of the sealing ring from an ambient atmosphere, prevent leakage and/or exclude contamination and/or moisture. The contact pads commonly may be located as a group on a surface of the substrate and the sealing ring commonly may surround the group.

The sealing ring may comprise at least one of an organic material, a silicone or a plastic material. Specifically, the at least one sealing ring may comprise at least one polymer, including the option of the polymer comprising at least one silicone material. Thus, the sealing ring may comprise at least one elastomer. The elastomer may comprise at least one silicone material, preferably at least one silicone and/or a silicone polymer. The elastomer preferably may comprise at least one silicone copolymer, preferably a copolymer of dimethylsiloxane, more preferably a copolymer of dimethylsiloxane and urea. For example, the elastomer may comprise at least one urea copolymer. The elastomer may be a thermoplastic elastomer or a cured elastomer. As a commercial example of a material or group of materials usable for the sealing ring, Geniomer® materials available by Wacker Chemie AG, Munich, Germany, may be used, which form a group of poly(dimethylsiloxane)-co-polyurea copolymers. As an example, Geniomer® 110, Geniomer® 145, or Geniomer® 345 or mixtures thereof may be used. In a cured state, the sealing ring generally may have a Shore A hardness of, e.g., 5 to 150, such as 10 to 100, 20 to 90, or 25 to 85. It shall be noted, however, that other materials and/or other hardness are feasible. The named range of hardnesses, however, turned out to be favorable for the specified purposes.

The sealing lip may have a maximum height perpendicular to a surface of the sensor of, e.g., 20 µm to 300 µm, such as 50 µm to 200 µm or 80 µm to 150 µm, e.g., 100 µm. Other thicknesses, however, are feasible.

The sealing ring may directly be applied to the substrate, which includes the option that the substrate is fully or partially covered by at least one insulating material, such as at least one insulating resin or resist, which generally may form part of the substrate.

The sealing ring specifically may be producible by applying a liquid or pasty sealing material to the substrate, including the option that the liquid or pasty sealing material is applied to at least one insulating material fully or partially covering the substrate and, thus, by definition may form part of the substrate itself. The liquid or pasty sealing material may be fully or partially hardened after application, such as by one or more of drying, the operation of at least one solvent removal, chemical hardening or polymerization, photo curing or other ways of hardening. After hardening, the formerly liquid or pasty sealing material still may have a deformable shape and/or still may be compressible, in order to provide the above-mentioned sealing properties and in order to be compressed when pressed onto a surface.

The sealing ring may have a shape exemplarily selected from the group consisting of: a circular shape, an oval shape, a polygonal shape, a rectangular shape. However, the sealing ring may generally have an arbitrary shape. Further, the sealing ring may generally have an arbitrary cross-section, such as a rectangular cross-section and/or rounded cross-section and/or a polygonal cross-section. However, other types of cross-sections may be applied alternatively.

The sealing ring may further have a constant thickness. Thus, the sealing ring may define a closed sealing line along which the sealing ring contacts and element such as a flat element onto which the substrate is pressed. Along this sealing line, the sealing ring may have a constant thickness, with a tolerance of variation of, e.g., no more than 20% or no more than 10%. However, other embodiments are feasible.

The sealing ring may comprise at least one sealing lip. Thus, in a cross-sectional view perpendicular to the sealing element and/or perpendicular to a surface of the sensor and/or the substrate, the sealing ring may define a cross-sectional profile with at least one, such as exactly one, maximum such as a local maximum. Thus, the profile may provide a maximum which defines the sealing lip. Thus, generally, as used herein, the term "sealing lip" may refer to a maximum in a cross-sectional profile of the sealing ring, which, when the sensor with the sealing ring thereon is pressed onto another surface, is the first part of the sealing ring to contact the other surface. The profile itself may be symmetric or asymmetric in shape, wherein an asymmetric profile may be favorable. Therein, the maximum height may be closer to an inner or outer perimeter of the sealing ring.

As further used herein, the term "body mount" generally refers to a device which is attachable to the skin of the user or patient. Thus, the body mount may comprise at least one attachment component which is capable of connecting the body mount to the skin, such as at least one adhesive surface and/or at least one adhesive strip or plaster. The body mount may further comprise at least one body mount housing which may be used as a sensor support, for attachment of the sensor, such as the contact portion of the sensor. Thus, generally, the body mount may also be referred to as a sensor support.

The sensor assembly, specifically the body mount, may further comprise at least one pressure element. The pressure element may be located in between a surface of the body mount and the sensor. The sensor assembly may be configured such that the sensor may be presses against the pressure element or vice versa during the transfer of the sensor form the initial position into the final position.

As used herein, the term "pressure element" refers to an arbitrary element which is configured for pressing one element onto another element or vice versa. Specifically, the pressure element may be one or both of flexible or deformable. Thus, the pressure element may comprise at least one flexible or deformable material, such as at least one layer of flexible and/or deformable material.

The pressure element may comprise at least one of: an elastomer; a foam; a textile; a spring element; a thermoplastic polymer. The pressure element may be located in between a surface of the body mount and the sensor. The pressure element may be part of the control part. Thus, specifically, the pressure element may be part of the body mount and/or may be attached to the body mount. The pressure element may be fully or partially integrated into a base of the body mount, such as by multicomponent injection molding. Additionally or alternatively, the pressure element may be attached to a surface of the sensor, specifically on a side of the sensor facing away from the electronics unit and/or from the electrical contacts of the electronics unit.

The pressure element may be located on a first side of the sensor, such as on a first side of the substrate of the sensor, and the sealing ring may be located on an opposing, second side of the sensor, such as of the substrate of the sensor. Therein, the pressure element may be attached to the sensor or may simply be pressed onto the sensor, whereas, as outlined above, the sealing ring is attached to the sensor. Thus, the pressure element and the sealing ring may be located on opposing sides of the sensor in the sensor assembly. Therein, the sealing ring may face the electronics unit and the electrical contacts, and the pressure element may be located facing away from the electronics unit.

The pressure element, on at least one surface, specifically on at least one surface facing the sensor, may comprise one or more cavities capable of acting as suction cups. The term "cavity" may refer to an arbitrary void volume within a surface, such as the surface of the pressure element. The cavities may be configured to adhere to an arbitrary surface, specifically by creating a partial vacuum. The partial vacuum may be created through a negative fluid pressure of a surrounding medium.

As further used herein, the term "insertion element" (also referred to herein as "inserter") generally refers to an arbitrary element which is configured to transfer the sensor to the body mount, such as by attaching the sensor to the body mount. For this purpose, the insertion element specifically may comprise at least one actuator and/or at least one plunger and/or at least one other tool which is adapted to bring the sensor into contact with the body mount, for, e.g., mechanical and/or electrical connection. Further, as will be outlined in detail below, the insertion element may simultaneously be configured to place at least one component at least partially into the body tissue of the user. Thus, the insertion element may be configured for fulfilling multiple functions, e.g., in addition to the transfer of the sensor to the body mount, the function of fully or partially inserting the sensor into the body tissue. Particularly, the insertion element may be configured to place the sensor at least partially into the body tissue of the user or patient. The insertion element may be configured such that a transfer of the sensor from the insertion element to the body mount, specifically to the pressure element of the body mount, may take place on insertion of a part of the sensor into the body tissue. The insertion element may be releasably connectable to the body mount. The insertion element, in a connected state, may be connected to the body mount in a predetermined angle. The insertion element may be configured for pressing the contact pads of the sensor onto the electrical contacts of an electronics unit, which will further be described below in more details, or vice versa.

The insertion element specifically may comprise at least one plunger, also referred to as a sled or a slider. The term "plunger" generally refers to an arbitrary element with at least one supporting surface configured to attach at least one element. The plunger may be fully or at least partially made of at least one plastic material. Specifically, the plunger may be manufactured by injection molding. The supporting surface may specifically be a smooth surface configured that an attachment of the at least one element, particularly of the sensor, to the supporting surface is encouraged. Specifically, the supporting surface may extend parallel to the body mount, specifically parallel to the pressure element of the body mount. The insertion element, specifically the plunger, may be configured such that a surface of the sensor is pressed on the body mount, particularly on the pressure element of the body mount, at an angle of 0° to 10°, more preferably 0° to 6°.

The plunger may be movable in a longitudinal direction via at least one actuator of the insertion element. The term "actuator" generally refers to an arbitrary element which is configured to move or control a mechanism or a system. The actuator may be operated by a source of energy, typically electric current or mechanical pressure and may convert energy into motion. The actuator may be a manually operable actuator. Other electromechanical actuators such as magnetic actuators, piezo actuators or other kind of actuators may be applied. The insertion element, specifically the actuator, may be configured to withdraw the plunger from the body mount after transfer of the sensor onto the body mount. The actuator may specifically be configured to move the plunger from the initial position to the final position.

The terms "initial position" and "final position" may refer to two different positions of the insertion element, specifically of the plunger, relative to the body mount. Thereby, the term "initial" may refer to a start position of the plunger during the method of mounting the sensor to the body mount. At this position the sensor attached to the plunger, specifically to the supporting surface of the plunger, may not contact the body mount, specifically the pressure element of the body mount. Thus, the initial position may also be referred to as upper position. The term "final" may refer to a terminal position of the plunger during the method of mounting the sensor to the body mount. At this position, the sensor may contact the body mount, specifically the pressure element of the body mount. Thus, the initial position may also be referred to as lower position. The method of mounting the sensor to the body mount may also comprise withdrawing the plunger from the body mount. Thereby, the actuator may be configured to move the plunger into a further upper position. The further upper position and the initial position may be identical. Thus, the terms "initial position" and "final position" may be considered as description without specifying an order and without excluding a possibility that the insertion element may be movable to several kinds of initial positions and final positions.

The sensor assembly, specifically the plunger of the insertion element, may further comprise at least one cannula. The term "cannula" may generally refer to an arbitrary element which may be insertable into the body tissue of the user, particularly in order to deliver or to remove body fluid or to transfer an element. Therefore, the cannula may specifically be a hollow tube or hollow needle. The cannula, e.g., may comprise at least one cross-section selected from the group consisting of: round, elliptical, U shaped, V shaped. Still, other embodiments are feasible. Specifically, the cannula may be a slotted cannula. The cannula may be configured to be inserted vertically or at an angle of 90° to 30° to the body tissue of the user.

The cannula may be mounted to the plunger in a fixed position. The cannula may emerge from a bottom side of the plunger next to the supporting surface. The sensor may be partially, specifically with at least one insertable portion, received in the cannula. In an embodiment, the shaft of the sensor may at least partially be received in the cannula and the contact portion of the sensor may be located outside of the cannula. Particularly, the contact portion of the sensor may be attached to the supporting surface of the plunger. The cannula may be removed from the body tissue of the user during withdrawal of the plunger.

The insertion element may comprise at least one guiding element. The guiding element may be attachable to the body mount, e.g., for the mounting of the sensor to the body mount, and may also be releasable from the body mount after attachment of the sensor to the body mount. The guiding element may be configured to guide the actuator in a linear fashion in order to transfer the sensor to the body mount. Thus, as an example, the guiding element may be or may comprise at least one guiding rail and/or at least one guiding rod which may be configured to guide the actuator in a linear fashion. Thus, as an example, the actuator, e.g., a plunger, may be linearly slidable in at least one guiding rail and/or by a at least one guiding rod. The guiding rail and/or the guiding rod may be coupled to the body mount for the transfer of the sensor to the body mount and/or for the insertion of the sensor into the body tissue and may be removed from the body mount afterwards.

The sensor assembly may additionally comprise at least one mechanical safety element. The term "safety element" generally refers to an arbitrary element which may be configured to hold a component in positon so that an undesired movement of the component is at least reduced or even completely suppressed. Specifically, the mechanical safety element may be configured to additionally secure the sensor to the insertion element, specifically to the plunger, during transport or storage. Further, the mechanical safety element may be configured to release the sensor before transferring the sensor onto the body mount. In an embodiment, the mechanical safety element may be non-reversibly openable for releasing the sensor before transmitting the sensor onto the body mount. The mechanical safety element may be located in a region of the contact portion or of the shaft of the sensor. Exemplarily, the mechanical safety element may comprise at least one hook.

The term "adhesive element" (also referred to herein as "adhesive") may generally refer to an arbitrary material or element configured to bind two or more surfaces together by adhesion, such that the two surfaces may resist separation. The two or more surfaces may be bound together in a reversible or in an irreversible manner. Each adhesive element may be or may comprise at least one adhesive material. The term "adhesive material" may comprise reactive and non-reactive adhesive materials. The reactive adhesive materials may be configured to chemically react and form covalent forces in order to harden. The non-reactive adhesive materials may bind to a surface by non-covalent forces.

The terms "first adhesive element" and "second adhesive element" may be considered as description without specifying an order and without excluding a possibility that several kinds of first adhesive elements and second adhesive elements may be applied. Further, additional adhesive elements such as third adhesive elements may be applied.

One or both of the first or second adhesive elements may comprise at least one material selected from the group consisting of: a polymer adhesive; a silicone-based adhesive; silicone material, preferably at least one silicone and/or a silicone polymer; a silicone base thermoplastic material; a silicone copolymer, preferably a copolymer of dimethylsiloxane, more preferably a copolymer of dimethylsiloxane and urea; an urea copolymer; at least one solvent-based acrylic pressure-sensitive adhesive, specifically at least one solvent-based acrylic material comprising at least one polymer based acrylic esters.

One or both of the first adhesive elements or of the second adhesive elements may comprise at least one pressure sensitive adhesive material. The term "pressure sensitive adhesive material" may generally refer to an arbitrary adhesive material which may form a bond when pressure is applied. Specifically, no solvent, water or heat may be needed to activate the pressure sensitive adhesive material. A degree of bond may be influenced by an amount of pressure which may be used to apply the pressure sensitive adhesive material to a surface. Particularly, the pressure sensitive adhesive material may be designed to form a bond and hold properly at room temperatures. Specifically, the pressure sensitive adhesive material may be designed to bind to a surface via molecular interactions such as van der Waals forces and/or other intermolecular forces. The pressure sensitive adhesive material may further have viscoelastic properties.

The first and the second adhesive elements may be configured to contact the sensor on opposing sides. Specifically, the first and second adhesive elements may contact the sensor on opposing sides in the contact portion of the substrate of the sensor. One of the first or second adhesive elements may be one or both of integrated into the pressure element or be attached to the pressure element.

The second adhesive element may be configured to provide a second adhesive force adhering the sensor to the insertion element. Specifically, the second adhesive element may be configured to attach the sensor to the plunger. In the initial position the sensor may be attached to the plunger via the second adhesive element. The sealing ring may be fully or partially identical with the second adhesive material.

The first adhesive element may be configured to provide a first adhesive force adhering the sensor to the body mount. The first adhesive force may exceed the second adhesive force.

The sensor assembly may further comprise at least one removable liner. The removable liner may fully or at least partially cover the first adhesive element. The removable liner may be removable manually or automatically for transfer of the sensor into the final position. The removable liner may be configured to conserve the adhesive property of the pressure element during storage. Exemplarily, the removable liner may comprise at least one foil, specifically a foil made of a plastic material.

The sensor assembly may further comprise at least one control part having at least one electronics unit for one or more of controlling the detection of the analyte or transmitting measurement data to another component. The control part, preferably the electronics unit of the control part, may comprise at least two electrical contacts which are electrically connected to the contact pads of the sensor. Further, the control part may further comprise the at least one body mount adapted for being mounted to the skin of the user.

As used herein, the term "control part" may generally refer to an arbitrary component of the sensor assembly, which is designed to actuate the sensor and/or record signals from the sensor and/or evaluate these signals in whole or part. The control part may be designed to mechanically hold the sensor and to electrically contact the sensor.

As used herein, the term "electronics unit" generally refers to an arbitrary device having at least one electronic component. Specifically, the electronics unit may comprise at least one electronic component for one or more of performing a measurement with the sensor, performing a voltage measurement, performing a current measurement, recording sensor signals, storing measurement signals or measurement data, transmitting sensor signals or measurement data to another device. Other embodiments of the electronic components are feasible. The electronics unit specifically may comprise at least one circuit board having disposed thereon at least one electronics component, such as at least one active and/or at least one passive component. The electronics unit may further comprise at least one housing which fully or partially surrounds the electronics component. The electronics unit may further comprise at least one of an integrated circuit, a microcontroller, a computer or an application-specific integrated circuit (ASIC). The electronics unit may specifically be embodied as a transmitter or may comprise a transmitter, for transmitting data. Specifically, the electronics unit may be reversibly and/or releasably connectable to the body mount. For this purpose, the control part, specifically the body mount, may comprise one or more locking mechanisms. Thus, the body mount may include a locking mechanism having at least one lever pivotably mounted to the body mount. Specifically, the lever may be pivotably attached to one end of the body mount. The lever may be permanently mounted to the body mount. By use of the lever, the electronics unit may be releasably locked to the body mount.

In a further aspect of this disclosure, a method of mounting a sensor for detecting at least one analyte in a body fluid to a body mount attachable to a body of a user is disclosed. Specifically, the sensor assembly according to any embodiment as described above or as will further be described below, may be used for conducting the method.

The method comprises the method steps as given in the independent claims and as listed as follows. The method steps may be performed in the given order. However, other orders of the method steps are feasible. Further, one or more of the method steps may be performed in parallel and/or in a timely overlapping fashion. Further, one or more of the method steps may be performed repeatedly. Further, additional method steps may be present which are not listed.

The method of mounting the sensor to the body mount comprises the following steps:
  providing the at least one sensor, wherein the sensor is an electrochemical sensor;
  providing the at least one body mount;
  providing at least one insertion element for transferring the sensor to the body mount;
  providing at least one first adhesive element attached to one or both of the body mount or the sensor, configured for attaching the sensor to the body mount;
  providing at least one second adhesive element attached to one or both of the sensor or the insertion element, configured for releasably attaching the sensor to the insertion element; and
  transferring the sensor from an initial position, in which the sensor is attached to the insertion element via the second adhesive element, into a final position in which the sensor is attached to the body mount via the first adhesive element and released from the insertion element, by using the insertion element.

The proposed sensor assembly for detecting at least one analyte in a body fluid as well as the proposed method of mounting a sensor for detecting at least one analyte in a body fluid to a body mount attachable to a body of a user provide many advantages over known devices and methods.

A sensor assembly may be provided, wherein the sensor assembly may specifically comprise reversible and multiple electrical contacts at a minimal construction volume while a sealing, specifically the sealing ring, is precisely positioned. In an exemplary embodiment, the sensor of the sensor assembly may be electrically connected to the electronics unit of the sensor assembly.

Advantages of the disclosed device and method may specifically be a cost-effective production and the possibility to apply surface mount technology component placement systems, specifically pick- and place systems, during manufacturing, which may be paralleled and may lead to a high throughput. Further, the sensor assembly may have a low weight, a low construction height of preferably <1 mm, more preferably <0.6 mm and particularly preferably <0.4 mm, and a low construction volume of preferably <25 mm$^3$, more preferably <12 mm$^3$ and particularly preferably <10 mm$^3$. Further, plugs and/or plastic parts on the sensor may not be necessary.

The sensor, specifically the electrochemical and transcutaneous sensor, may comprise the shaft and the contact portion. Particularly, the substrate of the sensor may comprise the shaft and the contact portion. The shaft may have an elongate shape. Specifically, the shaft may extend along a straight line. However, the shaft may be divergent from the straight line. The shaft may further have a uniform width or may have a variable width. The sensor may further comprise the electrical traces and the electrodes which may be deposited on the substrate. The substrate may specifically comprise an electrically insulating material. The electrodes may comprise the working electrode, the counter electrode and the reference electrode. The electrical traces may contact the electrodes to the contact pads, which may be located on the contact portion of the substrate. Furthermore, the electrical traces may be covered by the electrically insulating material.

The step of electrically connecting the sensor to the electronics unit may occur after placing the sensor at least partially within the body tissue of the patient or the user. In order to attach the electronics unit to the body tissue of the user or the patient, the body mount may be attached to the body tissue such as by the plaster. After placing the sensor at least partially within the body tissue the electronics unit may be mounted to the body mount mechanically. During this step, the electrical contacts of the electronics unit may be pressed against the contact pads of the sensor or vice versa. Furthermore, a sealing may be formed around the contact pads.

The step of placing the sensor at least partially within the body tissue of the user or patient may be conducted via the cannula, specifically via the slotted cannula, which may be inserted vertically or at an angle of 90° to 30° to the surface of the skin. The sensor may at least partially be received in the cannula. Specifically, the shaft of the sensor may be located within the cannula. The cannula may comprise at least one cross-section selected from the group consisting of: round, elliptical, U shaped, V shaped. Other embodiments are feasible. During withdrawal of the cannula from the body tissue the sensor may at least partially remain within the body tissue. Specifically, the sensor may remain within the body tissue except for the contact portion and parts of the electrical traces.

The cannula may be firmly attached to the plunger. The plunger may be fully or at least partially made of at least one plastic material. The plunger may be movable via the actuator, which may specifically be a spring actuator, from a first upper position to a lower position and from there back to a second upper position. The first upper position and the second upper position may be identical. The first upper position and the second upper position may correspond to the initial position as described above or as will further be described below. The lower position may correspond to the final position as described above or as will further be described below.

The insertion element may be releasably connected to the body mount with accurate positioning. The insertion element may comprise the at least one guiding element being configured for positioning the cannula and the sensor relative to the body mount with known tolerance. After placing the sensor at least partially within the body tissue of the user the insertion element may be disconnected from the body mount.

The contact portion of the sensor may be releasably connected to the plunger with accurate positioning. The step of attaching the contact portion of the sensor to the plunger may be conducted through precision grasping, moving and pressing via at least one vacuum gripper.

The releasable attachment of the sensor to the insertion element may be conducted via adhesion or via adherence. The adhesion may be conducted via a layer of an adhesive material. The adhesive material may be deposited on the bottom side of the plunger facing the contact portion of the sensor. The adherence may be conducted via the sealing ring. Surprisingly, it was found, that Geniomer® 345 or Geniomer® 145 or a mixture of both may have a high adhesive strength against the plunger of the insertion element when applied as sealing material, particularly such that the contact portion of the sensor may be hold in position. During tensile load orthogonal to the bottom side of the plunger the contact portion may be freed from the plunger. The bottom side of the plunger may particularly be a plane and may be parallel or at least almost parallel to the surface of the pressure element.

In order to secure the sensor, specifically the contact portion of the sensor, to the insertion element, specifically to the bottom side of the plunger, the mechanical safety element, particularly the hook, may be configured to support the attachment. Specifically, the mechanical safety element may be located in a region of the contact portion or of the shaft of the sensor. The mechanical safety element may be non-reversibly openable before the attachment of the contact portion to the insertion element is released, for example by irreversible swinging out or by bending of the hook.

At the base of the body mount the pressure element may be located which may be configured to exert pressure on the contact portion of the sensor. The pressure element may comprise at least one of an elastomer, a foam, a textile. Optionally, the pressure element may also comprise at least one spring element. Exemplarily, the pressure element may be made of a thermoplastic polymer and may be mounted onto the body mount via injection molding, particularly via two-component-injection molding.

During insertion of the cannula into the body tissue of the user the plunger may move into the lower position. The sensor assembly may comprise at least one catching element configured to improve a precision of positioning. Within the lower position the contact portion may be located between the surface of the pressure element and the bottom side of the plunger.

The surface of the pressure element may have adhesive properties. The removable liner may be configured to conserve the adhesive property of the pressure element during storage. The removable liner may be removable manually or automatically for transfer of the sensor into the lower position.

The first adhesive force of the first adhesive element located between the body mount, specifically the pressure element, and the sensor may exceed the second adhesive force of the second adhesive element located between the sensor and the insertion element. Therefore, the sensor may be released from the insertion element as soon as the plunger is moved from the lower position to the second upper position. To provide a reliable and precise transfer of the sensor, specifically the contact portion of the sensor, the surface of the pressure element and the bottom side of the plunger may be arranged to each other in an angle of 0° to 6°. Still, other embodiments are feasible. Alternatively, a folded foil may be fixedly located on the bottom side of the plunger. The foil may unfold during moving the plunger into the second upper position. During this step, the foil may be removed from the surface of the contact portion. The contact portion of the sensor may optionally be fixedly located on the pressure element via a mechanical safety element.

An adherence of the sensor to the surface of the pressure element may be provided through an adhesive material. Surprisingly, it was found that in case the pressure element was made of an elastomer, specifically of Geniomer® 345, a sufficiently high adhesive force may be existent to remove the contact portion of the sensor from the plunger. Additionally, the surface of the pressure element may comprise one or more of the cavities, particularly in form of a spherical segment. During pressing the contact portion onto the pressure element through the plunger air may be fully or at least partially removed from the cavities and the partial vacuum which may be created during releasing the plunger may lead to an additional holding force to the contact portion of the sensor. The removal of the air from the cavities may be facilitated in case the surface of the pressure element and the contact portion are oriented in a slight slanting position to each other.

Alternatively, the pressure element may be attached to the bottom side of the contact portion in an unremovable fashion. In this case, the pressure element may be pressed and attached onto the body mount via the plunger, in combination with the contact portion. Within such a configuration the attachment of the sensor to the body mount and the insertion may be conducted in a comparable way as described above with slight variations.

The insertion element may be removed from the body mount after inserting the sensor into the body tissue and the movement of the plunger into the second upper position. The electronics unit may be placed onto the body mount such that at least the last movement may be conducted at least almost vertically to the surface of the pressure element. Thereby, the contact portion may be compressed between the surface of the pressure element and the bottom side of the electronics unit such that the electrical connection as well as the sealing between the sensor and the electronics unit may form.

Summarizing the findings of this disclosure, the following embodiments are preferred:

Embodiment 1

A sensor assembly for detecting at least one analyte in a body fluid, comprising:
- at least one sensor, wherein the sensor is an electrochemical sensor;
- at least one body mount configured for attachment to a body of a user;
- at least one insertion element for transferring the sensor to the body mount;
- at least one first adhesive element attached to one or both of the body mount or the sensor, configured for attaching the sensor to the body mount;
- at least one second adhesive element attached to one or both of the sensor or the insertion element, configured for releasably attaching the sensor to the insertion element, wherein the insertion element is configured to transfer the sensor from an initial position, in which the sensor is attached to the insertion element via the second adhesive element, into a final position in which the sensor is attached to the body mount via the first adhesive element and released from the insertion element.

Embodiment 2

The sensor assembly according to the preceding embodiment, wherein the first and second adhesive elements are configured to contact the sensor on opposing sides.

Embodiment 3

The sensor assembly according to any one of the preceding embodiments, wherein the second adhesive element is configured to provide a second adhesive force adhering the sensor to the insertion element, wherein the first adhesive element is configured to provide a first adhesive force adhering the sensor to the body mount, wherein the first adhesive force exceeds the second adhesive force.

Embodiment 4

The sensor assembly according to any one of the preceding embodiments, wherein one or both of the first or second adhesive elements comprise at least one pressure sensitive adhesive.

Embodiment 5

The sensor assembly according to any one of the preceding embodiments, wherein one or both of the first or second adhesive elements comprise at least one material selected from the group consisting of: a polymer adhesive; a silicone-based adhesive; silicone material, preferably at least one silicone and/or a silicone polymer; a silicone-based thermoplastic material; a silicone copolymer, preferably a copolymer of dimethylsiloxane, more preferably a copolymer of dimethylsiloxane and urea; an urea copolymer; at least one solvent-based acrylic pressure-sensitive adhesive, specifically at least one solvent-based acrylic material comprising at least one polymer based on acrylic esters.

Embodiment 6

The sensor assembly according to any one of the preceding embodiments, wherein the insertion element is configured such that a transfer of the sensor from the insertion element to the body mount takes place on insertion of a part of the sensor into a body tissue.

Embodiment 7

The sensor assembly according to any one of the preceding embodiments, wherein the insertion element comprises at least one plunger, wherein the second adhesive element is configured to attach the sensor to the plunger.

Embodiment 8

The sensor assembly according to the preceding embodiment, wherein, in the initial position, the sensor is attached to the plunger via the second adhesive element.

Embodiment 9

The sensor assembly according to any one of the two preceding embodiments, wherein the plunger is movable in a longitudinal direction via at least one actuator of the insertion element.

Embodiment 10

The sensor assembly according to the preceding embodiment, wherein the actuator is a manually operable actuator.

Embodiment 11

The sensor assembly according to any one of the two preceding embodiments, wherein the insertion element comprises at least one guiding element attachable to the body mount, the guiding element being configured to guide the actuator in a linear fashion.

Embodiment 12

The sensor assembly according to any one of the five preceding embodiments, wherein the insertion element, specifically the actuator, is configured to withdraw the plunger from the body mount after transfer of the sensor onto the body mount.

Embodiment 13

The sensor assembly according to the preceding embodiment, wherein a cannula is removed from a body tissue of the user during withdrawal of the plunger.

Embodiment 14

The sensor assembly according to any one of the preceding embodiments, wherein the sensor assembly additionally comprises at least one mechanical safety element, preferably a hook, wherein the mechanical safety element is configured to additionally secure the sensor to the insertion element, specifically to the plunger, during transport or storage, wherein the mechanical safety element is configured to release the sensor before transferring the sensor onto the body mount.

Embodiment 15

The sensor assembly according to the preceding embodiment, wherein the mechanical safety element is non-reversibly openable for releasing the sensor before transferring the sensor onto the body mount.

Embodiment 16

The sensor assembly according to any one of the preceding embodiments, wherein the sensor assembly further comprises at least one pressure element located in between the surface of the body mount and the sensor, wherein the sensor assembly is configured such that the sensor is pressed against the pressure element or vice versa during the transfer of the sensor from the initial position into the final position.

Embodiment 17

The sensor assembly according to the preceding embodiment, wherein the pressure element is one or both of flexible or deformable.

Embodiment 18

The sensor assembly according to any one of the two preceding embodiments, wherein one of the first or second adhesive elements are one or both of integrated into the pressure element or attached to the pressure element.

Embodiment 19

The sensor assembly according to any one of the three preceding embodiments, wherein the pressure element comprises at least one of: an elastomer; a foam; a textile; a spring element; a thermoplastic polymer.

Embodiment 20

The sensor assembly according to any one of the four preceding embodiments, wherein the pressure element is fully or partially integrated into a base of the body mount, preferably by multicomponent injection molding.

Embodiment 21

The sensor assembly according to any one of the five preceding embodiments, wherein the pressure element is attached to a surface of the sensor.

Embodiment 22

The sensor assembly according to any one of the six preceding embodiments, wherein the pressure element, on at least one surface, comprises one or more cavities capable of acting as suction cups.

Embodiment 23

The sensor assembly according to any one of the preceding embodiments, wherein the insertion element is configured such that a surface of the sensor is pressed onto the body mount, preferably a pressure element of the body mount, at an angle of 0° to 10°, more preferably 0° to 6°.

Embodiment 24

The sensor assembly according to any one of the preceding embodiments, wherein the sensor assembly further comprises at least one electronics unit having at least one electronics component for one or more of controlling the detection of the analyte or transmitting measurement data to another component.

Embodiment 25

The sensor assembly according to the preceding embodiment, wherein the electronics unit is reversibly connectable to the body mount.

Embodiment 26

The sensor assembly according to any one of the preceding embodiments, wherein the sensor assembly further comprises at least one removable liner, wherein the removable liner fully or partially covers the first adhesive element, wherein the liner is removable for transfer of the sensor into the final position.

Embodiment 27

The sensor assembly according to any one of the preceding embodiments, wherein the insertion element further comprises at least one cannula, specifically at least one slotted cannula, wherein the sensor partially, specifically with at least one insertable portion, is received in the cannula.

Embodiment 28

The sensor assembly according to any one of the preceding embodiments, wherein the insertion element is releasably connectable to the body mount.

Embodiment 29

The sensor assembly according to the preceding embodiment, wherein the insertion element, in a connected state, is connected to the body mount in a predetermined angle.

Embodiment 30

The sensor assembly according to any one of the preceding embodiments, the sensor having at least one substrate, the sensor further having at least two electrodes applied to the substrate, the electrodes being adapted for detecting the analyte, the sensor further having at least two contact pads applied to the substrate and at least two electrical traces applied to the substrate, the electrical traces electrically connecting the electrodes and the contact pads.

Embodiment 31

The sensor assembly according to the preceding embodiment, wherein the sensor further comprises a sealing ring fixedly applied to the substrate, the sealing ring surrounding the contact pads.

Embodiment 32

The sensor assembly according to the preceding embodiment, wherein the sealing ring is fully or partially identical with the second adhesive element.

Embodiment 33

The sensor assembly according to any one of the two preceding embodiments, wherein the contact pads are commonly located as a group on a surface of the substrate, wherein the sealing ring commonly surrounds the group.

Embodiment 34

The sensor assembly according to any one of the three preceding embodiments, wherein the sealing ring has a constant thickness.

Embodiment 35

The sensor assembly according to any one of the four preceding embodiments, wherein the sealing ring is fixedly connected to the substrate by material engagement.

Embodiment 36

The sensor assembly according to any one of the five preceding embodiments, wherein the sealing ring comprises at least one polymer.

Embodiment 37

The sensor assembly according to any one of the six preceding embodiments, wherein the sealing ring comprises at least one elastomer.

Embodiment 38

The sensor assembly according to the preceding embodiment, wherein the elastomer comprises at least one silicone material, preferably at least one silicone and/or a silicone polymer.

Embodiment 39

The sensor assembly according to any one of the two preceding embodiments, wherein the elastomer comprises at least one silicone copolymer, preferably a copolymer of dimethylsiloxane, more preferably a copolymer of dimethylsiloxane and urea.

Embodiment 40

The sensor assembly according to any one of the three preceding embodiments, wherein the elastomer comprises at least one urea copolymer.

Embodiment 41

The sensor assembly according to any one of the four preceding embodiments, wherein the elastomer is a thermoplastic elastomer or a cured elastomer.

Embodiment 42

The sensor assembly according to any one of the eleven preceding embodiments, wherein the sealing ring comprises at least one sealing lip.

Embodiment 43

The sensor assembly according to the preceding embodiment, wherein the sealing lip is located on one or both of an inner or outer perimeter of the sealing ring.

Embodiment 44

The sensor assembly according to any one of the two preceding embodiments, wherein the sealing lip is spaced apart from the substrate.

Embodiment 45

The sensor assembly according to any one of the fourteen preceding embodiments, wherein the sealing ring has a shape selected from the group consisting of: a circular shape, an oval shape, a polygon shape, a rectangular shape an arbitrary shape.

Embodiment 46

The sensor assembly according to any one of the fifteen preceding embodiments, wherein the sensor further comprises at least one electrically insulating material, preferably an insulating resist, the electrically insulating material at least partially covering the electrical traces, the insulating material leaving open the electrodes and the contact pads, wherein the sealing ring at least partially is applied to the insulating material.

Embodiment 47

The sensor assembly according to any one of the sixteen preceding embodiments, wherein the sealing ring is producible by applying a liquid or pasty sealing material to the substrate.

Embodiment 48

The sensor assembly according to the preceding embodiment, wherein the liquid or pasty sealing material is hardened after application.

Embodiment 49

The sensor assembly according to any one of the preceding embodiments, wherein the sensor comprises at least one working electrode having at least one test chemical being sensitive to the analyte to be detected.

Embodiment 50

The sensor assembly according to the preceding embodiment, wherein the working electrode further comprises at least one conductive working electrode pad, wherein the conductive working electrode pad is in contact with the at least one test chemical.

Embodiment 51

The sensor assembly according to any one of the preceding embodiments, wherein the sensor comprises at least one counter electrode.

Embodiment 52

The sensor assembly according to any one of the preceding embodiments, wherein the sensor comprises at least one reference electrode.

Embodiment 53

The sensor assembly according to any one of the two preceding embodiments, wherein the counter electrode and the reference electrode are one of a common electrode or two separate electrodes.

Embodiment 54

The sensor assembly according to any one of the preceding embodiments, wherein the sensor comprises at least one substrate.

Embodiment 55

The sensor assembly according to the preceding embodiment, wherein the substrate is a flexible substrate, preferably a substrate comprising at least one foil, more preferably a substrate comprising at least one polyimide foil.

Embodiment 56

The sensor assembly according to any one of the two preceding embodiments, wherein the substrate is an elongate substrate, with electrodes being placed at one end of the elongate substrate and contact pads being placed on an opposing end of the substrate.

Embodiment 57

The sensor assembly according to the preceding embodiment, wherein the substrate comprises at least one contact portion, wherein the contact pads are located in the contact portion.

29

Embodiment 58

The sensor assembly according to the preceding embodiment, wherein the contact portion is widened as compared to the remaining substrate.

Embodiment 59

The sensor assembly according to any one of the two preceding embodiments, wherein the contact portion is a rectangular contact portion.

Embodiment 60

The sensor assembly according to any one of the three preceding embodiments, wherein the first and second adhesive elements contact the sensor on opposing sides in the contact portion.

Embodiment 61

The sensor assembly according to any one of the preceding embodiments, wherein the insertion element is configured for pressing contact pads of the sensor onto the electrical contacts of the electronics unit or vice a versa.

Embodiment 62

A method of mounting a sensor for detecting at least one analyte in a body fluid to a body mount attachable to a body of a user, comprising:
- providing the at least one sensor, wherein the sensor is an electrochemical sensor;
- providing the at least one body mount;
- providing at least one insertion element for transferring the sensor to the body mount;
- providing at least one first adhesive element attached to one or both of the body mount or the sensor, configured for attaching the sensor to the body mount;
- providing at least one second adhesive element attached to one or both of the sensor or the insertion element, configured for releasably attaching the sensor to the insertion element; and
- transferring the sensor from an initial position, in which the sensor is attached to the insertion element via the second adhesive element, into a final position in which the sensor is attached to the body mount via the first adhesive element and released from the insertion element, by using the insertion element.

Embodiment 63

The method according to the preceding embodiment, wherein the sensor assembly according to any one of the preceding embodiments referring to a sensor assembly is used.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
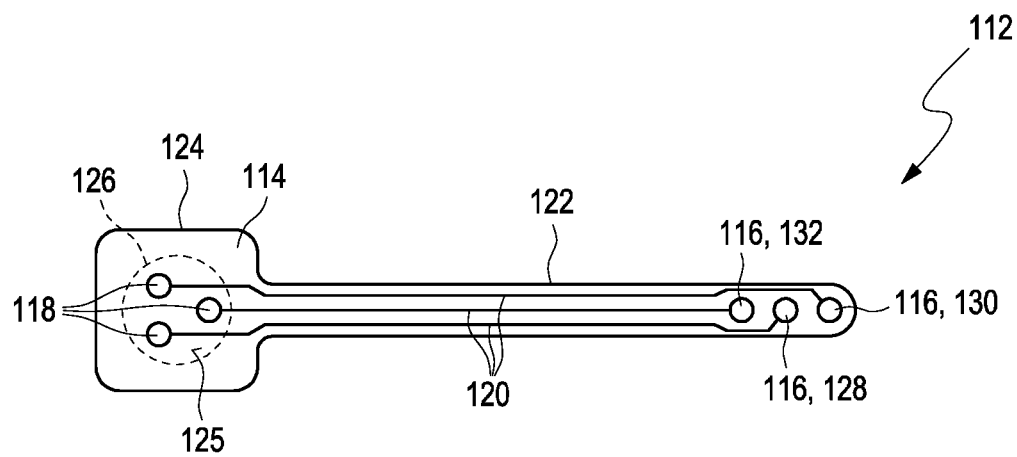
FIGS. 1A and 1B show an exemplary embodiment of a sensor for detecting at least one analyte in a body fluid and of a method of manufacturing the same.
Figure 1:
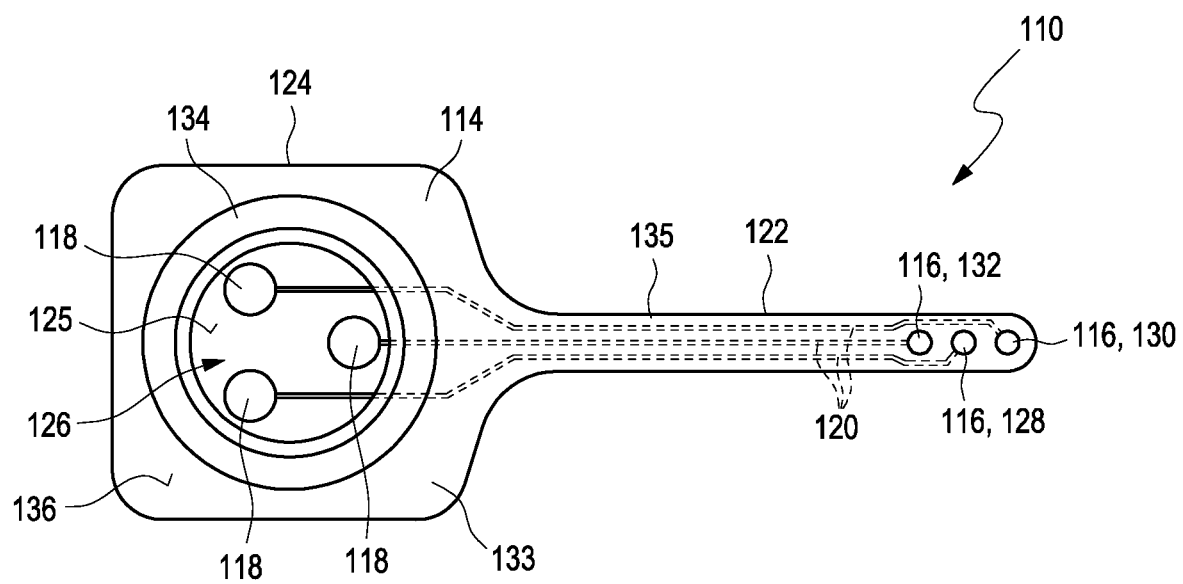

In FIGS. 1A and 1B, an exemplary embodiment of a sensor 110 for detecting at least one analyte in a body fluid and of a method of manufacturing the same are shown. FIG. 1A shows an intermediate product 112 of the sensor 110, whereas the sensor 110 is illustrated in FIG. 1B. However, other embodiments of the sensor 110 are feasible.

In a first step, as shown in FIG. 1A, at least one substrate 114 may be provided, at least two electrodes 116 may be applied to the substrate 114, at least two contact pads 118 may be applied to the substrate 114 and at least two electrical traces 120 may be applied to the substrate 114. For potential techniques for application of these elements 116, 118 and 120, reference may be made to the disclosure above and/or to conventional techniques used for manufacturing circuit boards, specifically flexible circuit boards. Elements 116, 118 and 120 may fully or partially be applied in a single step or in separate steps. Various embodiments are feasible, as the skilled person will recognize.

The substrate 114, which specifically may be or may comprise a flexible substrate such as a flexible foil, specifically may comprise a shaft 122 and a contact portion 124. The shaft 122 may have an elongate shape. The contact portion 124 may be widened as compared to the remaining substrate 114. As an example, the contact portion 124 may be a rectangular contact portion 124. The substrate 114 may be a flexible substrate 114. For example, the substrate 114 may comprise at least one polyimide foil.

The electrical traces 120 preferably may have an elongated shape. Further, the electrical traces 120 may fully or partially be located on the shaft 122 of the substrate 114. The electrical traces 120 may electrically interconnect the contact pads 118 and the electrodes 116. The electrical traces 120 may comprise at least one electrically conductive material. Exemplarily, the electrical traces 120 may comprise copper. However, other embodiments are feasible, as outlined in further detail above.

The contact pads 118 may be located inside a contact surface area 126, which may be a surface area covering the contact pads 118. In FIG. 1A the contact surface area 126 is symbolically depicted by a dashed circle. Particularly, the contact surface area 126 may have a circular and/or rectangular shape.

The contact pads 118, as outlined above, may be fully or at least partially made of a metallic material. Specifically, the contact pads 118 may comprise at least one gold layer. The contact pads 118 may be located in the contact portion 124.

The electrodes 116 may comprise at least one working electrode 128 adapted for performing at least one electrochemical detection reaction for detecting the at least one analyte in the body fluid. The working electrode 128 may have at least one test chemical being sensitive to the analyte to be detected. As an example, the at least one test chemical may be deposited on top of a working electrode pad which has electrically conductive properties. Further, the electrodes 116 may comprise at least one counter electrode 130 adapted for performing at least one electrochemical counter reaction adapted for balancing a current flow required by the detection reaction at the working electrode 128. Additionally, the electrodes 116 may further comprise at least one reference electrode 132 which may have a stable and well-known electrode potential. It shall be noted, however, that other electrode setups may be feasible, such as setups having more than three electrodes or less than three electrodes, such as by combining the counter electrode 130 and the reference electrode 132. It also may be feasible to have at least one of the electrodes 116 and at least one of the electrical traces 120 and at least two of the contact pads 118 applied to a first side of the substrate 114 and have at least one of the electrodes 116 and at least one of the electrical traces 120 applied to a second side of the substrate 114 and connected with at least one contact pad 118 on the first side by at least one via. Thus, generally, a more complex geometry or a more complex layer setup of the sensor 110 is generally feasible, such as a layer setup having electrical traces 120 in different planes of the layer setup and, as an example, using contact pads 118 on different sides and/or using vias for providing electrical contact between one or more of the contact pads 118 and one or more of the electrical traces 120.

In a second step, as illustrated in FIG. 1B, at least one electrically insulating material 133 may be applied to the substrate 114. In case at least one insulating material 133 may be applied to the substrate 114, the electrically insulating material 133 itself, after application, may form part of the substrate 114. Thus, in the context of this disclosure, when reference is made to applying one or more elements to the substrate 114, the one or more elements may directly be applied to the substrate 114 or may be applied to the substrate 114 with the insulating material 133 disposed thereon.

For example, the electrically insulating material 133 may comprise an insulating resist. However, other materials are feasible. The electrically insulating material 133 may at least partially cover the electrical traces 120, the electrically insulating material 133 leaving open the electrodes 116 and the contact pads 118. Particularly, the electrically insulating material 133 may comprise at least one insulating cover layer 135 covering the electrical traces 120.

Further, at least one sealing ring 134 may be applied fixedly to the substrate 114. The sealing ring 134 may be fully or partially applied onto the electrically insulating material 133. The sealing ring 134 may exceed the electrically insulating material 133 in height. Particularly at least one insulating layer 136 may be formed by the electrically insulating material 133.

The step of applying the sealing ring 134 may comprise applying at least one sealing material, preferably in a liquid or pasty form, to the substrate 114. The contact pads 118 may be commonly located as a group on a surface 125 of the substrate 114 and the sealing 134 may commonly surround the group. The sealing material may specifically comprise at least one solvent and may further comprise at least one matrix material, such as one of a polymer material, a plastic material or a precursor material capable of cross-linking or polymerizing. The step of applying the sealing ring 134 may comprise at least one application method, such as a dosing method, e.g., a dispensing method. Further, the step of applying the at least one sealing ring 134 may comprise at least one curing step. Consequently, in the curing step, the sealing material may be fully or partially hardened.

The substrate 114 was manufactured by utilizing a polyimide foil with a thickness of 50 μm from Contag AG, Berlin, Germany. The contact portion 124 of the substrate 114 had dimensions of 5 mm×5 mm. The electrical traces 120 were made of copper. Additionally, the electrical traces 120 were galvanized with gold plating. The contact pads 118 and the electrodes 116 were also galvanized with gold plating. The electrical traces 120, the contact pads 118 and the electrodes 116 had an average thickness of 18 μm respectively. The contact pads 118 had an average diameter of 0.6 mm. The electrical traces 120 and the substrate 114 were isolated via the insulating layer 136, which had an average thickness of about 28 μm. The contact surface area 126 had an average diameter of 2.4 mm.

The sealing material was manufactured as follows: 4.357 g of Geniomer® 145 from Wacker Chemie AG were dissolved in 13.43 g of isopropyl alcohol at 80° C. while stirring for 8 hours. After that, the sealing material was filtered by using a syringe filter with an average pore size of 5.0 μm from Whatman, GE-Healthcare UK Limited, Little Chalfont, UK. A slightly turbid solution was received.

The sealing material was put into a 1 ml syringe and the sealing material was deposited onto the contact portion 124 of the substrate 114 as a closed ring via a dosing needle Tip 23 GA.013X.5 Orange 50 PC from GLT, Pforzheim, Germany. The sealing material was dried at 80° C. for 2 hours. After drying, the sealing ring 134 had an average thickness of around 45 μm.

Figure 2:
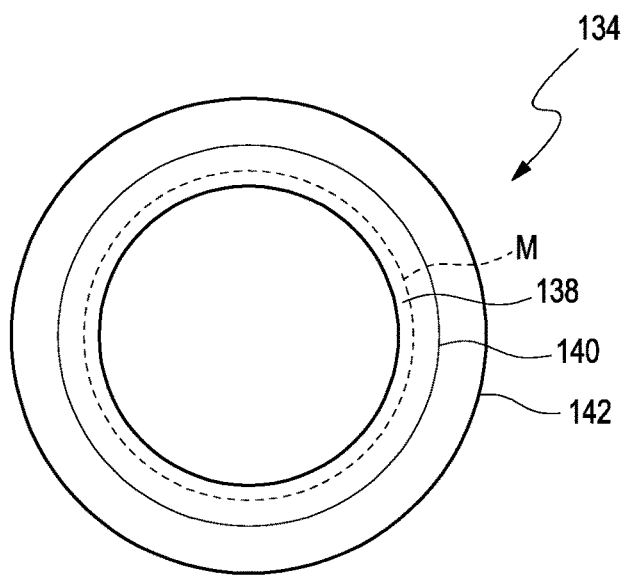
FIGS. 2A to 2C show an exemplary embodiment of a sealing ring in a top view (FIG. 2A) and in a cross-sectional view (FIG. 2B), and a height profile measurement of the sealing ring (FIG. 2C)
Figure 2:
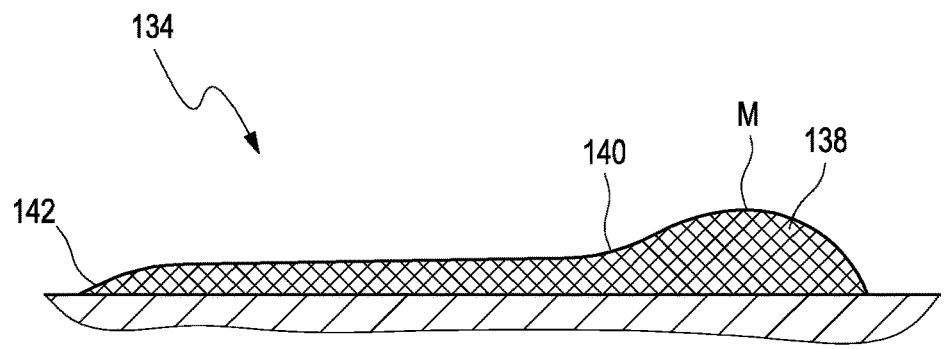
Figure 2:
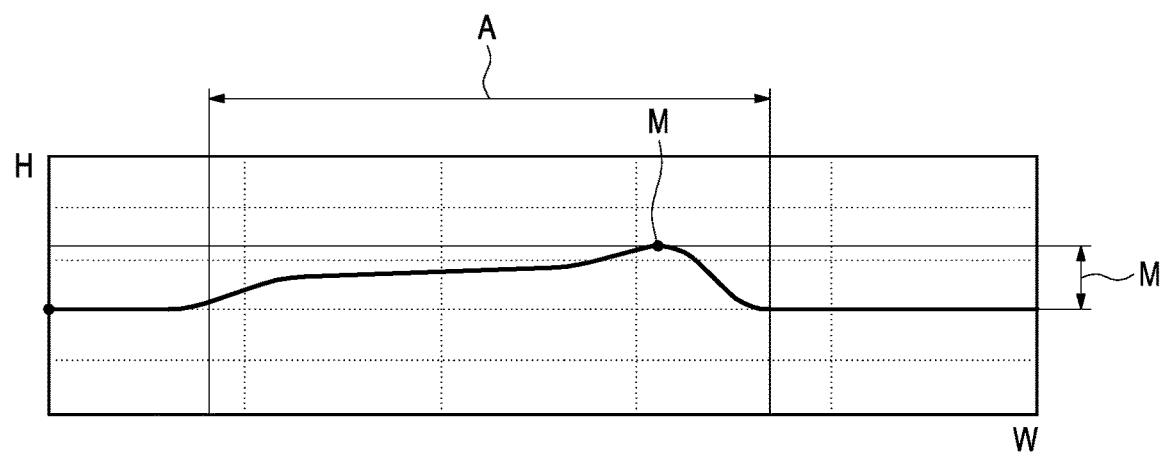

FIGS. 2A to 2C show details of an exemplary embodiment of the sealing ring 134 in various views. Thus, FIG. 2A shows a top view. FIG. 2B shows a cross-sectional view in a plane perpendicular to a surface of the substrate 114 of the sensor 110, oriented radially in the sealing ring 134. FIG. 2C shows a high-profile measurement of the sealing ring 134, also in the plane of the cross-sectional view of FIG. 2B.

The sealing ring 134 as depicted in FIGS. 2A and 2B exemplarily may be manufactured by the method as described above, such as by dispensing. The sealing ring 134 may have a circular shape. Specifically, the sealing ring 134 may have a constant thickness over its circumference. Thus, as depicted in FIGS. 2A to 2C, the points M of maximum height 134 may form a circular or noncircular closed sealing line, which is denoted symbolically by the dashed circle M in FIG. 2A. Along this sealing line, the sealing ring 134 may have a constant thickness. It shall be noted, however, that other embodiments are feasible. Furthermore, the sealing ring 134 may comprise at least one sealing lip 138, which is formed by the local maximum M in the height profile, as seen in FIGS. 2B and 2C. In this embodiment, the sealing lip 138 may be located closer to the inner perimeter 140 of the sealing ring 134 then to the outer perimeter. Thus, the profile of the sealing ring 134 generally may be asymmetrical. Alternatively, however, other profiles are feasible, such as symmetrical profiles or profiles with the sealing lip 138 being located on the outer perimeter 142 of the sealing ring 134.

The sealing ring 134 may comprise at least one silicone material such as an elastomeric silicone material. Particularly, the sealing ring 134 may be designed to be compressed during assembly between two or more elements.

In experiments, 30% to 50% solutions of Geniomer® (Geniomer® 145 or Geniomer® 345) from Wacker Chemie AG, Munich, Germany, dissolved in isopropyl alcohol were deposited onto the substrate 114 via a dosing method. The substrate 114 was manufactured by utilizing a polyimide foil. Further, the substrate 114 comprised the insulating layer 136. As dosing needles Tip 27 GA GP.008x.25 CLEAR and Tip 25 GA GP.010x.25 RED from Nordson EDF, Westlake Ohio, USA, with an outer diameter of 0.4 mm or 0.5 mm respectively and an inner diameter of 0.203 mm or 0.254 mm respectively were applied. The dosing pressure was 2.0 bar to 4.0 bar and the velocity of the dosing needles was 2.6 mm/s to 5.0 mm/s. The diameter of application was 3.0 mm. One or two circulations of the dosing needles were conducted. The sealing ring 134 had a round shape and comprised the sealing lip 138 with a height ranging from 55 µm to 170 µm. Generally, the height of the sealing lip 138 increased with the volume of the dosed sealing material.

Further, when the sealing material was deposited along a straight line, it was found that after the curing step the sealing ring 134 comprised two sealing lips 138 located on both of the inner perimeter 140 and the outer perimeter 142 sides of the sealing ring 134. Consequently, the sealing material generally behaves according to the so called coffee-ring or coffee-stain effect. Generally, the coffee-ring or coffee-stain effect may also be observed in case a spherical shaped drop of a 25% solution of Geniomer® 145 dissolved in isopropyl alcohol with a diameter of around 3.5 mm is dried. In this case, however, a distinctive bead close to a rim of the drop was observed. In contrast, a drop which is deposited as a thin layer may generally dry without forming a distinctive bead. Therefore, surprisingly, it was found that a sealing lip 138 located on the inner perimeter 140 of the sealing ring 134 was formed by applying the elastomeric solution as sealing material.

In FIG. 2C an exemplary embodiment of potential dimensions of the sealing ring 134 is shown. Therein, a horizontal axis, denoted by W, is an axis which radially extends with respect to the sealing ring 134, parallel to a surface of the substrate 114. The vertical axis in FIG. 2C, denoted by H, shows the local height of the sealing ring 134. As can be seen in this high profile, in this embodiment, the width A of the sealing ring 134 may be in the range of, e.g., 400 µm to 700 µm, such as 560 µm, and the maximum height M may be in the range from 50 µm to 80 µm, preferably 65 µm. However, other dimensions are generally feasible.

Figure 3:
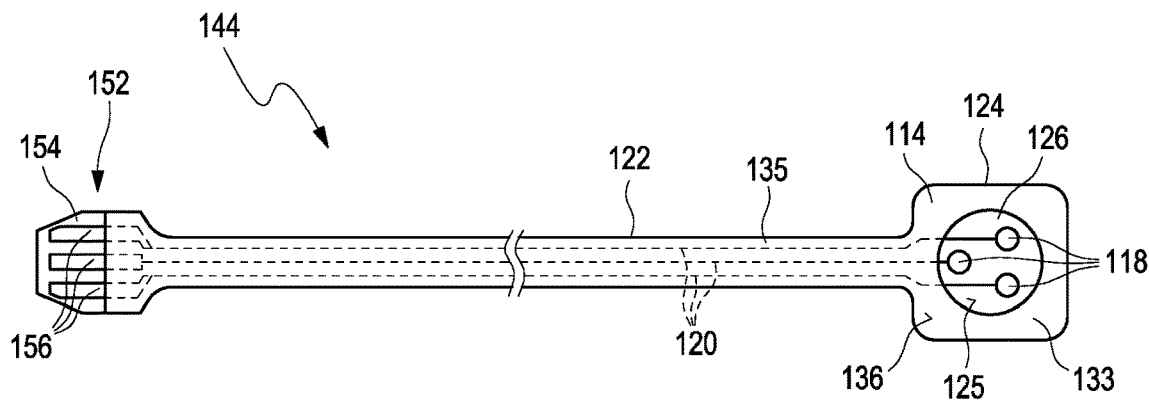
FIGS. 3A to 3D show various components of an exemplary testing setup for testing the sealing performance of the sealing ring, including a dummy test element for simulating a sensor (FIG. 3A), a first circuit diagram of an electrical setup for measuring an electrical resistance of the contact pads (FIG. 3B), a second circuit diagram of an electrical setup for measuring a vibration resistance (FIG. 3C) and a third circuit diagram of an electrical setup for measuring an insulation resistance (FIG. 3D)
Figure 3:
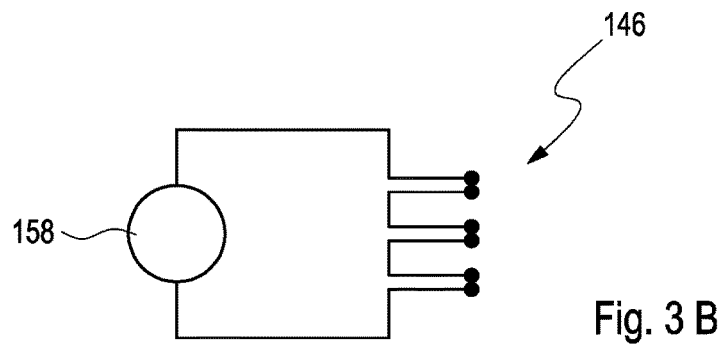
Figure 3:
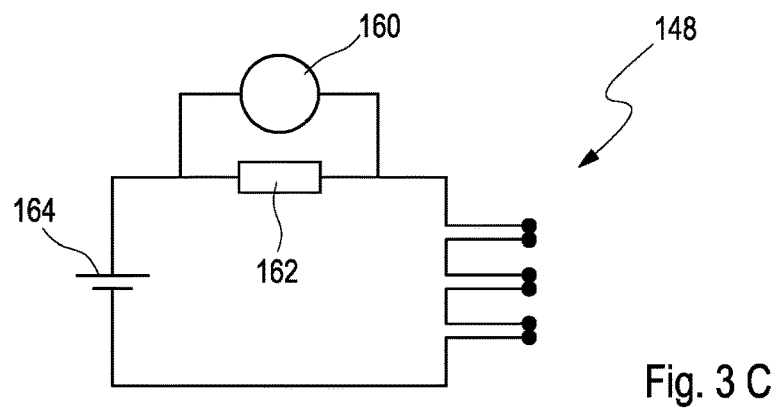
Figure 3:
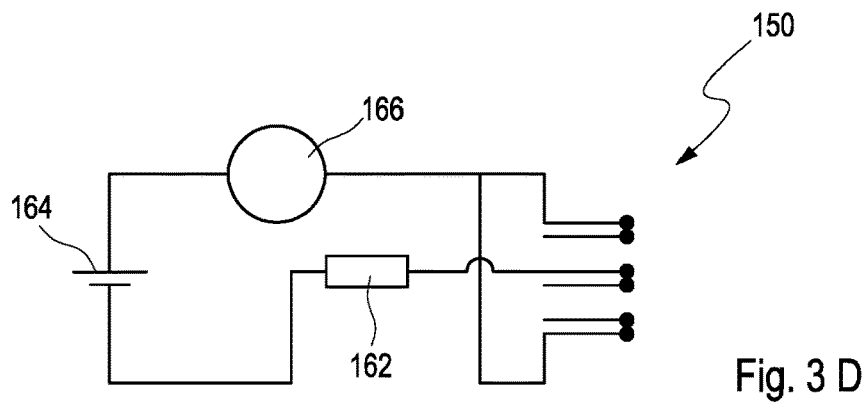

FIGS. 3A to 3D show various components of an exemplary testing setup for testing the sealing performance of the sealing ring 134. The testing setup specifically may comprise an exemplary test element 144, also referred to as a dummy test element or a dummy sensor, (FIG. 3A), an electrical setup according to a first circuit diagram 146 for measuring an electrical resistance of the contact pads 118 (FIG. 3B), an electrical setup according to a second circuit diagram 148 for measuring a vibration resistance (FIG. 3C) and an electrical setup according to a third circuit diagram 150 for measuring an insulation resistance (FIG. 3D).

The test element 144 as illustrated in FIG. 3A specifically may comprise the substrate 114 comprising the shaft 122 and the contact portion 124, as in a real sensor 110. The shaft 122 specifically may have a length in the range from 20 mm to 70 mm, preferably 50 mm. On one end 152 opposing the contact portion 124 the substrate 114 may comprise a further contact portion 154. The further contact portion 154 may comprise counter contact pads 156. The counter contact pads 156 may be connected to the contacts pads 118. Further, the counter contact pads 156 may be strip-shaped. However, other embodiments are feasible.

For measuring the electrical resistance, the electrical setup according to the first circuit diagram 146 as depicted in FIG. 3B may be applied. The contact pads 118 as depicted in FIG. 3A may be connected to an ohmmeter 158. In this embodiment, all contact pads 118, as illustrated in FIG. 3A, may be connected in series.

For measuring the vibration resistance of the contact pads 118, the electrical setup according to the second circuit diagram 148 as depicted in FIG. 3B may be applied. The second circuit diagram 148 specifically may comprise at least one voltmeter 160, at least one electrical resistor 162 and at least one voltage source 164.

For measuring the insulation resistance, the electrical setup according to the third circuit diagram 150 as depicted in FIG. 3D may be applied. The third circuit diagram 150 specifically may comprise at least one micro-ammeter 166, an electrical resistor 162 and the voltage source 164.

The shaft 122 of the substrate 114 had an average length of around 50 mm. Two test elements 144 were placed opposing each other, particularly the contact pads 118 of the two test elements 144 were placed opposing each other. A maximal discrepancy of ±0.2 mm was tolerated. The two test elements 144 were mechanically secured by applying adhesive strips onto the shaft 122, particularly in a distance of 3 mm to 5 mm to the contact portion 124. Specifically, the two test elements 144 were mechanically secured on a plate. The plate was made of polycarbonate and had a thickness of 2 mm and dimensions from 5 mm×5 mm.

As ohmmeter 158 a Fluke 117 multimeter was applied. As voltmeter 160 an oscilloscope TDS3034 from Tektronix, Beaverton, Oreg., USA was applied. As microammeter, a Keithley 2400 Sourcemeter, Kethley Instruments Inc., Cleveland, Ohio, USA was applied.

Figure 4:
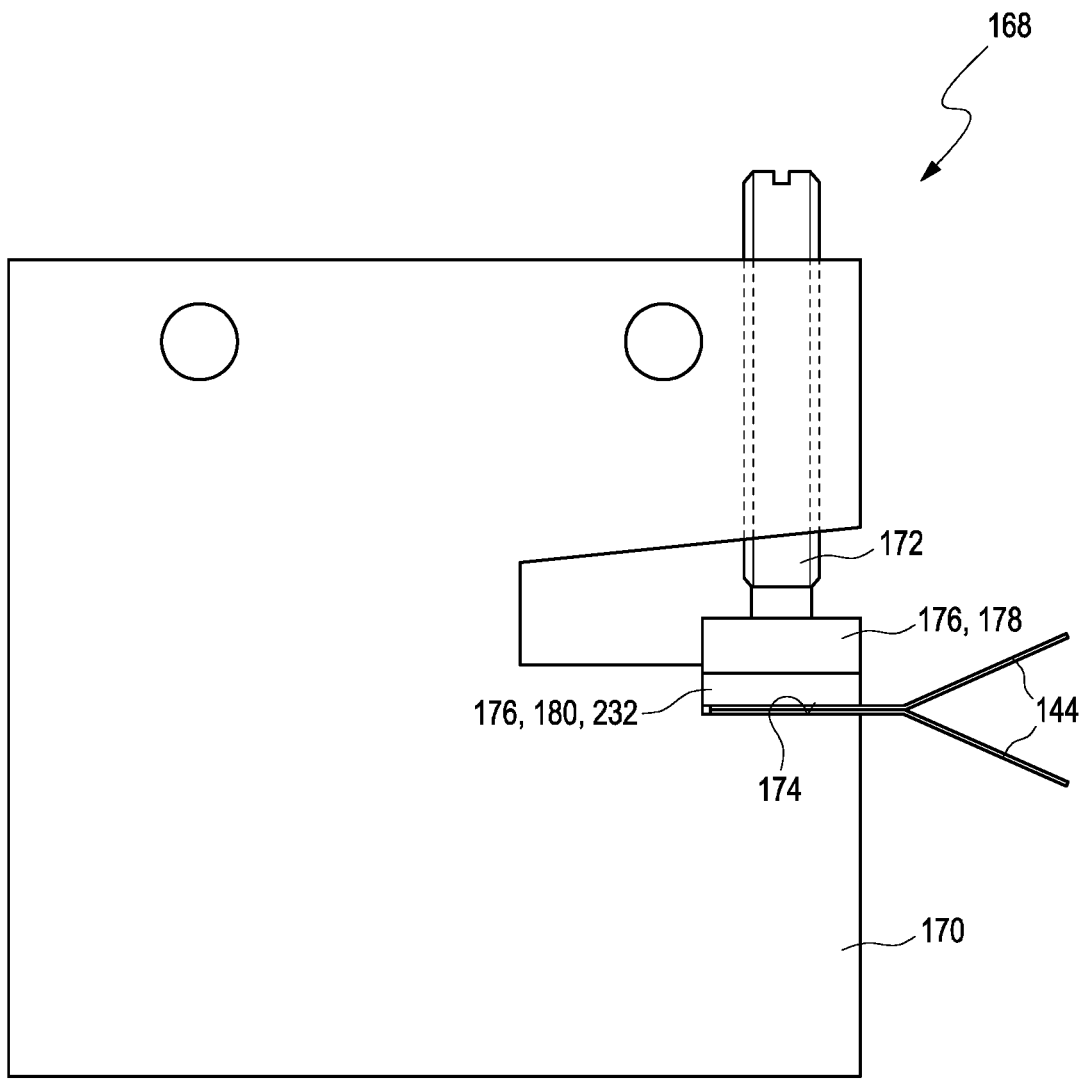
FIGS. 4A to 4C show an exemplary testing setup for testing a sealing ring (FIG. 4A) and schematic representations of an electrical connection between contact pads of a sensor and electrical contacts of an electronics unit without applying pressure (FIG. 4B) and with applying pressure by using a pressure element (FIG. 4C)

For testing the functionality of the sealing ring 134, a simulation testing setup was used, which is schematically shown in FIGS. 4A to 4C. Therein, in FIG. 4A, the testing setup is denoted by reference number 168. For the testing purposes, two test elements 144 as depicted, e.g., in FIG. 3A were used, and their contacts portions 124 were pressed together. In FIGS. 4B and 4C, enlarged cross-sectional views of the contact portions 124 are shown, without applying pressure (FIG. 4B) and with applying pressure to the upper one of the two test elements 144 by using a pressure element 232 (FIG. 4C). With this setup, an electrical connection between contact pads 118 of the sensor 110 and electrical contacts of the electronics unit 186 may be simulated. In order to simulate this situation, only the upper one of the two test elements 114 was configured to comprise a sealing ring 134, and, thus, simulates the sensor 110, whereas the lower one of the test elements 114 did not comprise any sealing ring 134 and, thus, simulates the electronics unit 186.

In FIG. 4A the testing setup 168 is depicted. The testing setup 168 comprises at least one terminal block 170 and at least one clamping screw 172. Between a supporting surface 174 of the terminal block 170 and the clamping screw 172, two plates 176 are located. The plates 176 comprise a first plate 178 in mechanical contact with the clamping screw 172 and a second plate 180 attaching to the first plate 178. The first plate 178, in this setup, is a hard plastic plate, whereas the second plate 180 comprises a deformable material such as an elastomeric material, e.g., a foam, and, thus, acts as a pressure element 232.

The two test elements 144 are located in between the pressure element 232 and the supporting surface 174 and each are electrically contacted in order to perform electrical performance tests, such as by using the electrical setups shown in FIGS. 3B to 3D.

As discussed above in the context of FIG. 3A, the test elements 144 each comprise the substrate 114 and the contact pads 118. The substrates 114 each are covered with the electrically insulating material 133 which, thus, forms part of the substrate 114. In the upper test element 144 in FIGS. 4B and 4C, the sealing ring 134 is positioned on top of the electrically insulating material 133.

As shown in FIG. 4B, representing the state without applying pressure by using the clamping screw 172, the sealing ring 134 comprises the sealing lip 138 which, as the first portion of the sealing ring 134, contacts the lower test element 144. As shown in FIG. 4C, once a force 184 is applied by using the clamping screw 172, the pressure element 232 exerts a pressure onto the upper test element 144. The sealing ring 134 is compressed, and the region in the center of the sealing ring 134 is fully or partially bent downward, towards the lower test element 144. As a consequence, the contact pads 118 of the upper test element 144 are pressed onto the corresponding contact pads 118 of the lower test element 144 and an electrical connection is formed, which can be tested with one or more of the setups shown in FIGS. 3B to 3D.

In order to test the functionality of the pressure element 232, the measurement may also be conducted by applying only the first plate 178, leaving out the deformable second plate 180. Similarly, in order to test the functionality of the sealing ring 134, experiments in which none or both of the test elements 144 may comprise the sealing ring 134. Further, the first plate 178 may be removed from the testing setup 168 and pressure may be applied via a finger of a user. Thereby, the performance of the sealing ring 134 and/or of the pressure element 232 may be tested in various ways.

In an experiment, two contact portions 124 of the two test elements 144 were placed on top of each other without the sealing ring 134. A first plate 176 was placed on top of the two test elements 144. Only when the applied force 184 was at least 20 N an electrical contact between the two test elements 144 was observed.

In a further experiment, the first plate was removed and pressure was applied via the finger onto the contact portions 124 of the two test elements 144. An electrical resistance of <1.1 Ohm was observed starting from an estimated value of 1 N to 2 N.

In a further experiment, the second plate 180 was made of Geniomer® 345 from Wacker Chemie AG, Munich, Germany and the second plate 180 had dimensions of 6 mm×6 mm×1 mm. The first plate 178 was made of polycarbonate, had dimensions of 5 mm×5 mm×2 mm and was placed on top of the second plate 180. An electrical resistance of <1.1 Ohm was observed starting from an estimated value of 2.2 N.

In a further experiment, the test elements 144 comprised sealing rings 134. Herein, the previous experiment was repeated. The second plate 180 was made of Geniomer® 345 from Wacker Chemie AG, Munich, Germany and the second plate 180 had dimensions of 6 mm×6 mm×1 mm. The first plate 178 was made of polycarbonate, had dimensions of 5 mm×5 mm×2 mm and was placed on top of the second plate 180. An electrical resistance of <1.1 Ohm was observed starting from an estimated value of 4 N to 5 N.

In a further experiment, the testing setup 168 as described above was applied. The second plate 180 was made of Geniomer® 345 from Wacker Chemie AG, Munich, Germany and the second plate 180 had dimensions of 6 mm×6 mm×1 mm. The first plate 178 was made of polycarbonate, had dimensions of 5 mm×5 mm×2 mm and was placed on top of the second plate 180. A force of around 8 N was applied via the clamping screw 172. The electrical setup according to the second circuit diagram 148 for measuring a vibration resistance as depicted in FIG. 3C and as described above was applied. It was observed, that an electrical connection existed between all contact pads 118. Further, vibrations of 50 Hz with an amplitude of around 1 mm were applied via a solenoid core. No interruptions of the electrical connection between the contact pads 118 were observed.

Further, the electrical setup according to the third circuit diagram 150 for measuring an insulation resistance as depicted in FIG. 3D was utilized and the testing setup 168 as depicted in FIG. 4A was applied. A voltage of 10 V was applied and a current was measured between two single contact pads 118 respectively. A maximal resolution of 0.00001 μA was reached. As a principle uncertainty of plus or minus one digit existed, it may be assumed, that the current had a maximal value of 0.00002 μA. A value for the isolation resistance between two contact pads 118 was determined to 1 Tera-Ohm. The experiment was continued for 21 days at room temperature and the isolation resistance was measured continuously. Thereby, a test solution of PBS buffer and 0.024% of sodium dodecyl sulfate was applied, so that the first plate 178, the second plate 180 and the two test elements 144 were floated with the test solution at 30 mm water column. Comparing to the initial state, no changes were observed. To make sure, that the high isolation resistance was not attributed to an error with the electrical traces 120, the contact pads 118 were released within the test solution and the sealing was lifted. At the moment of lifting the sealing, a maximal current was observed. Therefore, it was demonstrated, that the sealing ring 134 is able to conserve the isolation resistance of 1 Tera-Ohm over a period of a least 21 days.

Figure 5:
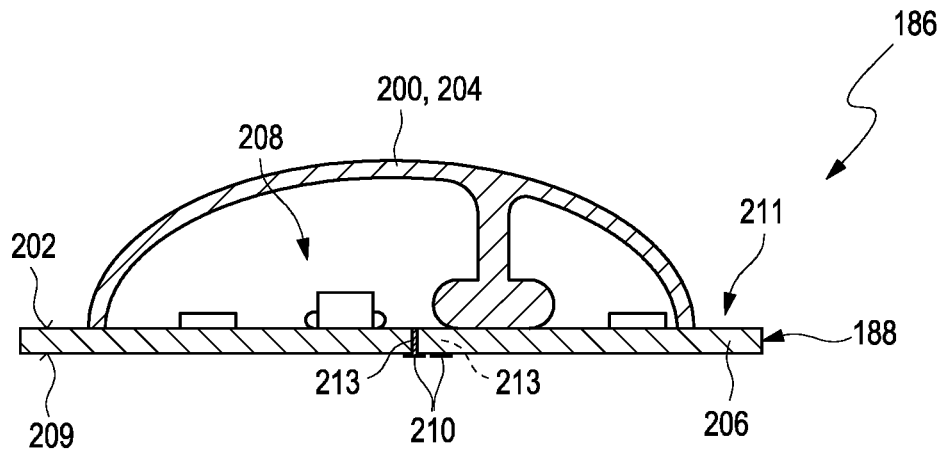
FIGS. 5A to 5B show an exemplary embodiment of an electronics unit of a sensor assembly in a cross-sectional view (FIG. 5A) and in a bottom view (FIG. 5B)
Figure 5:
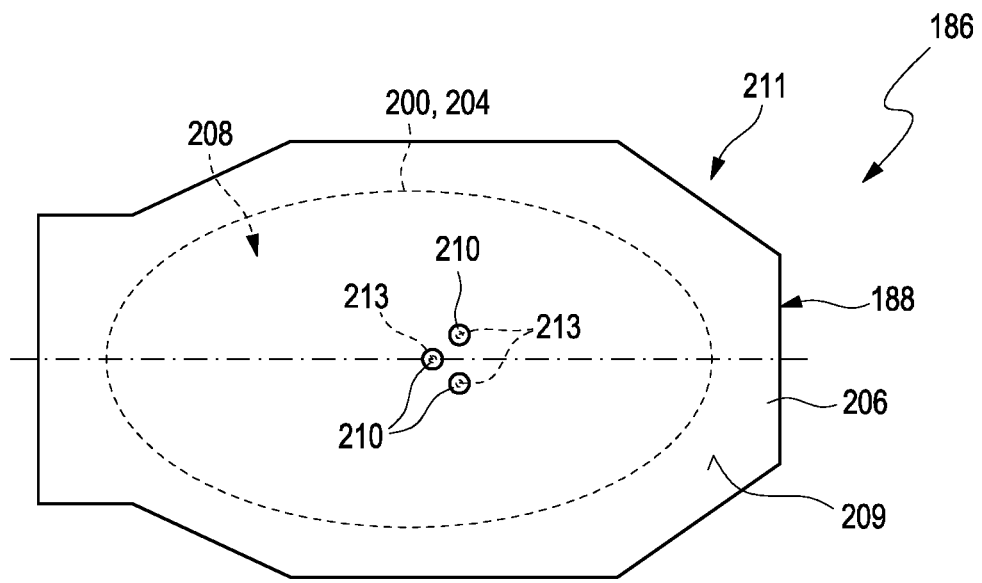
Figure 6:
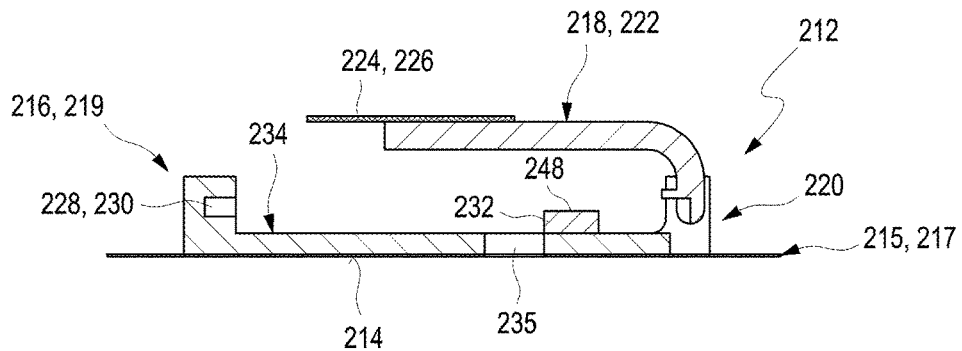
FIGS. 6A to 6D show components of an exemplary embodiment of a body mount of a control part of a sensor assembly.
Figure 6:
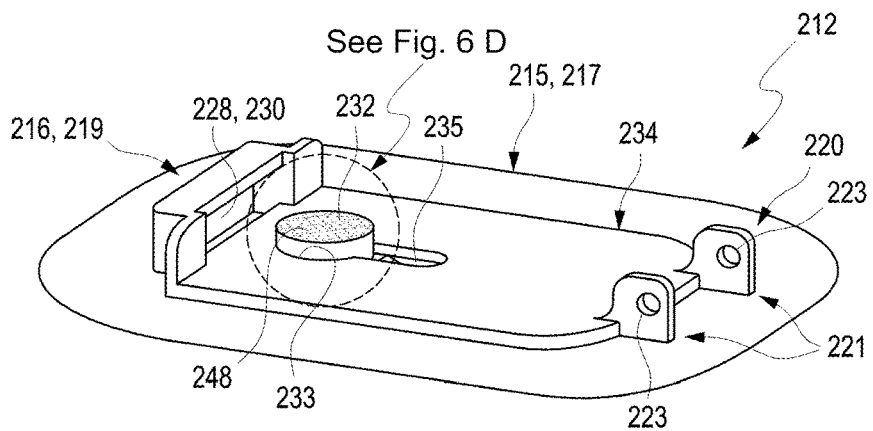
Figure 6:
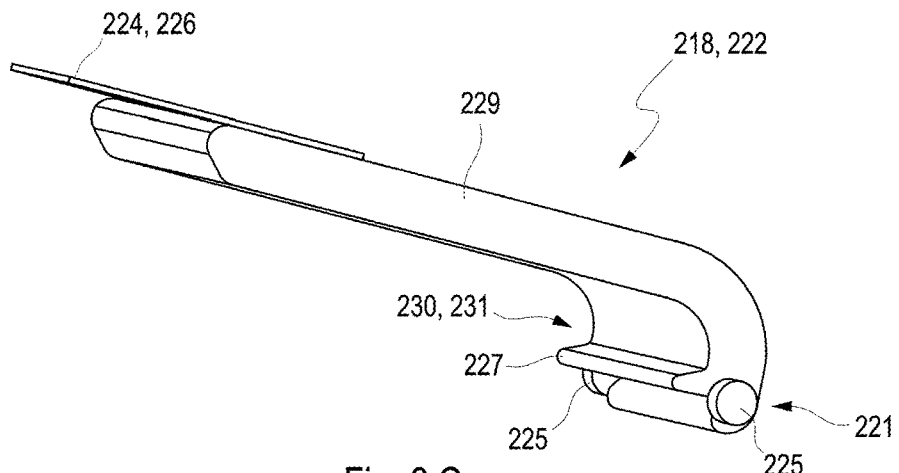
Figure 6:
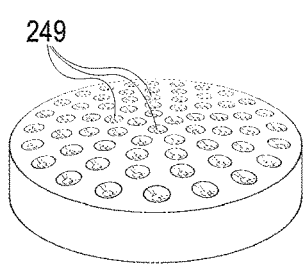

FIG. 5A and FIG. 5B show an electronics unit 186 of a sensor assembly 256 (shown below in FIGS. 9A to 10B). The electronics unit 186 may form part of a control part 254 of the sensor assembly 256 and may interact with a body mount 212, which will be shown below in FIGS. 6A to 6C.

FIG. 5A shows a cross-sectional view of the electronics unit 186, and FIG. 5B shows a bottom view thereof.

The electronics unit 186 may comprise an essentially flat base 188 and a housing 200 covering the base 188 on an upper side 202 opposing a body mount, which will further be described below in more detail. The housing 200 preferably may be a watertight housing 204 having an essentially round shape. The base 188 may protrude from the housing 200 on at least one side, thereby forming a protruding rim 206 on at least one side of the electronics unit 186. The protruding rim 206 may protrude on one side only or may fully or partially surround the electronics unit 186 and, as will be explained in further detail below, may be used for mounting the electronics unit 186 to a body mount 212, as will be further described below. Specifically, the protruding rim 206 may form part of a guiding structure for mounting the electronics unit 186 to the body mount 212 and, thus, may also be referred to as a "second guiding structure" 211, and interacting with a first guiding structure 230 of the body mount 212, as will be further discussed below in the context of FIGS. 9A to 10B.

The housing 200 may fully or at least partially cover the electronics unit 186 and may provide protection against mechanical influences and moisture. Specifically, the electronics unit 186 may comprise one or more electronics components 208, which are fully or partially covered by the housing 200.

The electronics unit 186, such as by using one or more of the electronics components 208, specifically may be configured for one or more of controlling the detection of the analyte or transmitting measurement data to another component, such as a receiver outside the sensor assembly. Therein, a wireless or a wire bound transmission may take place.

The electronics unit 186, for contacting the sensor 110 as will be explained in further detail below, may comprise at least two electrical contacts 210. The electrical contacts 210 may be electrically connected to the contact pads 118 of the sensor 110, as described above and as described in further detail below in the context of, e.g., FIGS. 9A to 10B, once the electronics unit 186 is mounted to the body mount 212. The electrical contacts 210 may be located on a lower side 209 of base 188 and may be electrically connected to one or more of the electronics components 208 inside the housing 200 by vias 213. Thus, as an example, the base 188 may be or may comprise one or more circuit boards, such as one or more printed circuit boards, such as one or more rigid printed circuit boards, and the vias 213 may penetrate the printed circuit board from the lower side 209, facing the body mount 212, to the upper side 202, facing the interior of the housing 200. The one or more electronics components 208 may be applied to the printed circuit board on the upper side 202. Further, one or more electrical leads or traces may be applied to the printed circuit board. It shall be noted, however, that other setups of the electronics unit 186 are feasible.

FIGS. 6A to 6D show an exemplary embodiment of a body mount 212 of the sensor assembly 256 in a cross-sectional view (FIG. 6A) as well as in partial perspective views of components of the body mount 212 (FIGS. 6B and 6C).

The body mount 212 may be configured for attachment to a body of a user. The body mount 212 may comprise a base 234 as depicted in FIG. 6B in a perspective view, and a lever 218 as depicted in FIG. 6C in a perspective view. The sensor assembly 256 will further be discussed below in more detail in the context of FIGS. 9A to 10B.

The body mount 212 may comprise at least one mounting element 217 for mounting the body mount 212 to the skin of the user. In the exemplary embodiment shown in FIGS. 6A and 6B, the mounting element 217 may comprise at least one plaster 215 having an adhesive surface 214 which may be adhered to the skin of the user. The plaster 215 may have an arbitrary shape, for example a rectangular shape or an oval shape. However, other embodiments are feasible. The adhesive surface 214 may be provided with a protective liner (not shown) which may be removed before adhering the adhesive surface 214 to the skin of the user.

Further, the body mount 212 may comprise a receptacle 228 on a side opposing the lever 218. The receptacle 228 may be capable of receiving a part of the electronics unit 186. As an example, the receptacle 228 may receive the protruding rim 206 of 188 of the electronics unit 186 or a part thereof, which, as outlined above, may act as a second guiding structure 211, as explained above in the context of FIGS. 5B and 5B. The body mount 212 may comprise a first guiding structure 230, and the receptacle 228 may form part of this first guiding structure 230.

Further, the body mount 212, particularly the base 234, may include a locking mechanism 216 having at least one lever 218 pivotably mounted to the body mount 212. Specifically, the lever 218 may be attached to one end 220 of the body mount 212, such as to one end of the base 234. The lever 218 may be permanently or removably mounted to the body mount 212. The lever 218, as an example, may be or may comprise a knee lever 222. A flexible extension 224, specifically a foldable foil 226, may be fixed to an outer end of the lever 218, capable of being gripped by a user for opening the lever 222.

The locking mechanism 216 specifically may be a self-locking mechanism 219. As explained in further detail above, the self-locking may be induced in such a way that, when the electronics unit 186 is inserted into the body mount 212, the electronics unit 186 exerts a force onto the lever 218 which holds the lever in a closed state or closed position. Thus, as will be explained in the context of FIG. 10B below, the locking mechanism 216 may have an open state or open position, such as when the lever 218 is opened or pivoted in a vertical position, in which the electronics unit 186 may be taken out of the body mount 212. When the electronics unit 186 is inserted into the body mount 212, the lever 218 may be pivoted in a horizontal position, as will be shown in the context of FIG. 10A below, in which the locking mechanism 216 is in a closed state or closed position. In this closed state or closed position, the electronics unit 186 may exert a force onto the lever 218 which holds the lever 218 in the closed position.

For this purpose, the lever 218, as depicted in FIG. 6C, may be shaped in a specific way. The lever 218 is connected to the base 234 of the body mount 212 by a hinge 221, comprising, e.g., sleeves 223 on the body mount 212 and corresponding studs 225 on the lever 218, such that the lever 218 may be pivoted. The lever 218 specifically may be designed as a knee-lever 222, having a protrusion 227 which faces inwardly. The protrusion, in conjunction with a main lever arm 229 of the lever 218, may form a further receptacle 231, into which, as depicted in FIG. 10B below, the rim 206 or a part thereof of base 188 may be inserted. The receptacle 231 may also form part of the first guiding structure 230 of the body mount 212.

The first guiding structure 230 and the second guiding structure 211 of the electronics unit 186 as illustrated within FIGS. 5B and 5B may be configured to interact such that the electronics unit 186 may be positioned relative to the body mount 212 in a state in which the electronics unit 186 is locked to the body mount 212.

Further, a pressure element 232 may be integrated into the base 234 of the body mount 212, such as by adhering the pressure element 232 to the base 234 and/or by integrating the base 234 with the pressure element 232 by multicomponent injection molding. The pressure element 232 may be integrated into a cavity 233 of the base 234 as depicted in FIG. 6B. The pressure element 232 may be one or both of flexible or deformable. Particularly, the pressure element 232 may comprise at least one of: an elastomer; a foam; a textile; a spring element; a thermoplastic polymer. Exemplarily, the pressure element 232 may be made of Geniomer® 345 from Wacker Chemie AG, Munich, Germany. The pressure element 232 may have an arbitrary shape. For example, the pressure element 232 may have a cylindrical shape. However, other embodiments are feasible. As shown in FIG. 6D, which is an enlarged view of part of the pressure element 232, the pressure element may have on at least one surface facing the sensor, one or more cavities 249 capable of acting as suction cups. The body mount 212 may further comprise at least one opening 235 which fully penetrates the body mount 212, specifically the base 234 and the adhesive surface 214. The opening 235 may be located next to the pressure element 232. The opening 235 may exemplarily have a round or a rectangular cross-section. However, other embodiments are feasible. As explained in further detail below, such as in the context of FIGS. 8B, 8C, 8D, 9A or 10B, the opening 235 may be used for guiding the cannula 242 and/or the sensor 110 into the body tissue and, thus, the cannula 242 and/or the shaft 122 of the sensor 110 may pass through the opening 235.

Figure 7:
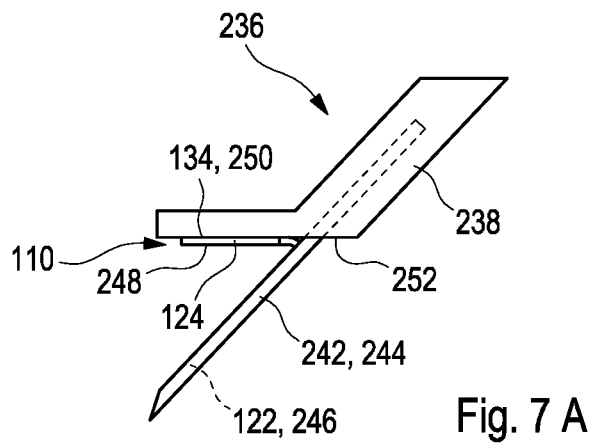
FIGS. 7A to 7C show different embodiments of an insertion element.
Figure 7:
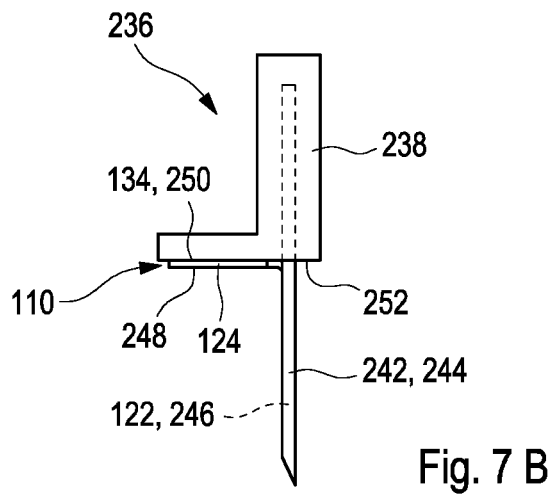
Figure 7:
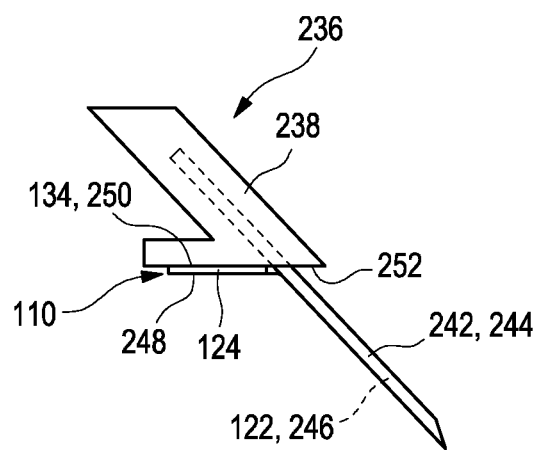
Figure 8:
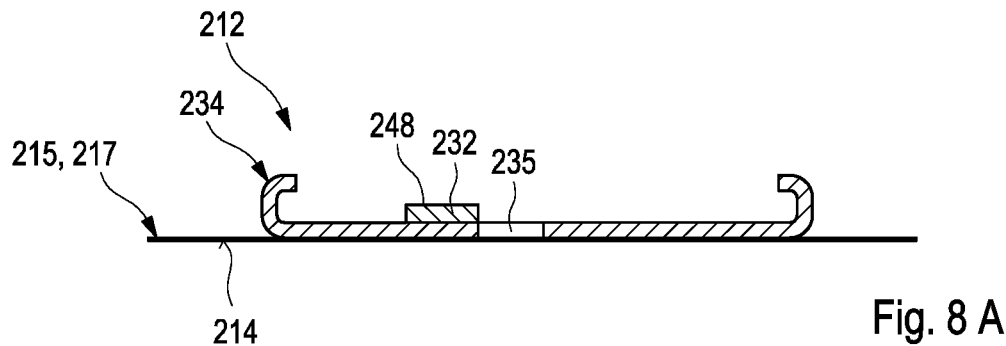
FIGS. 8A to 8D show a method of mounting a sensor to a body mount.
Figure 8:
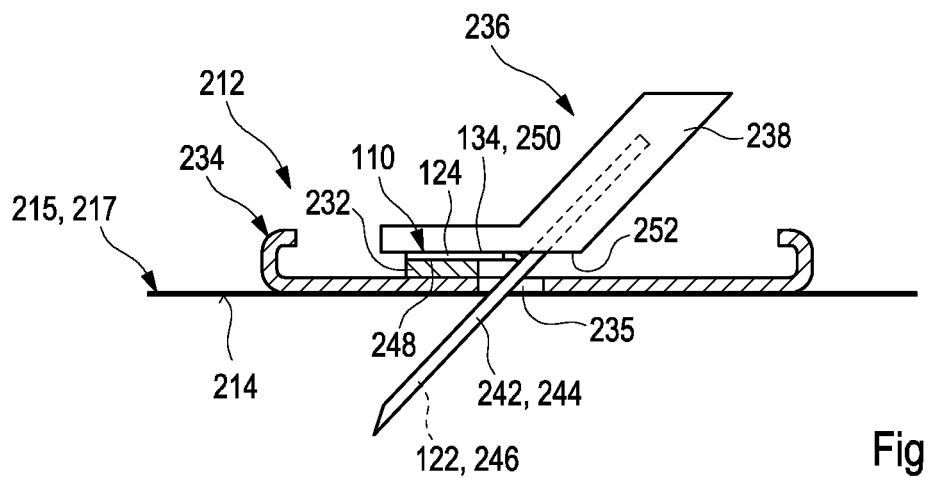
Figure 8:
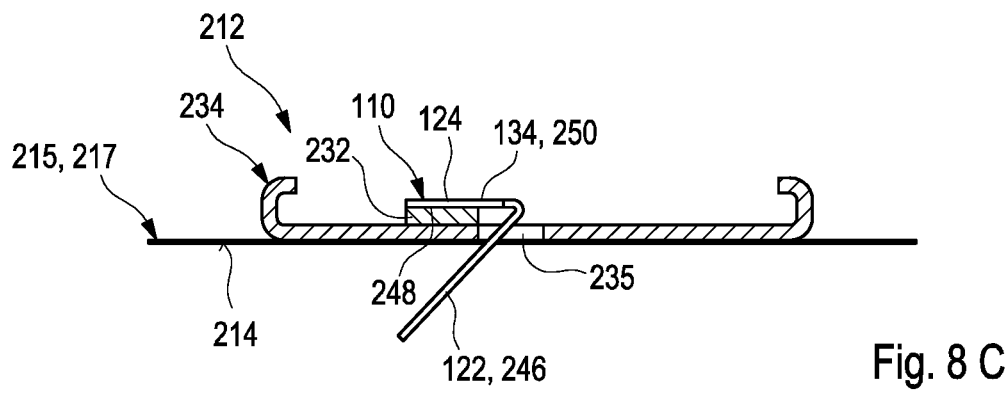
Figure 8:
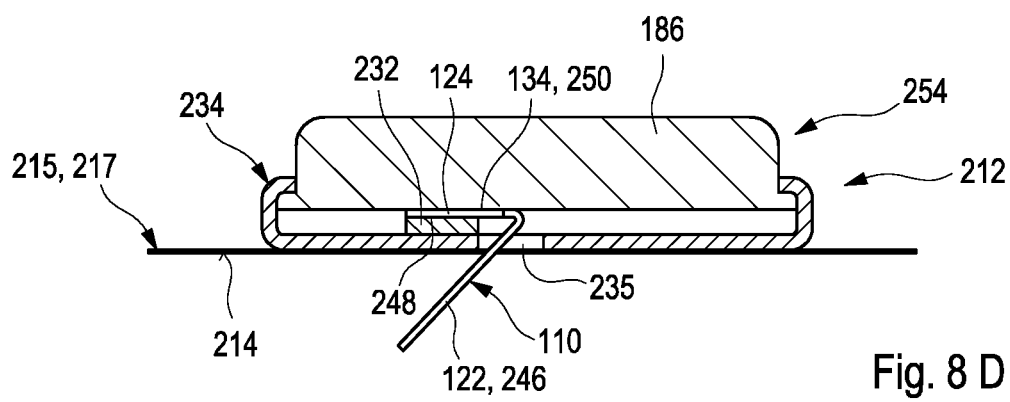
Figure 9:
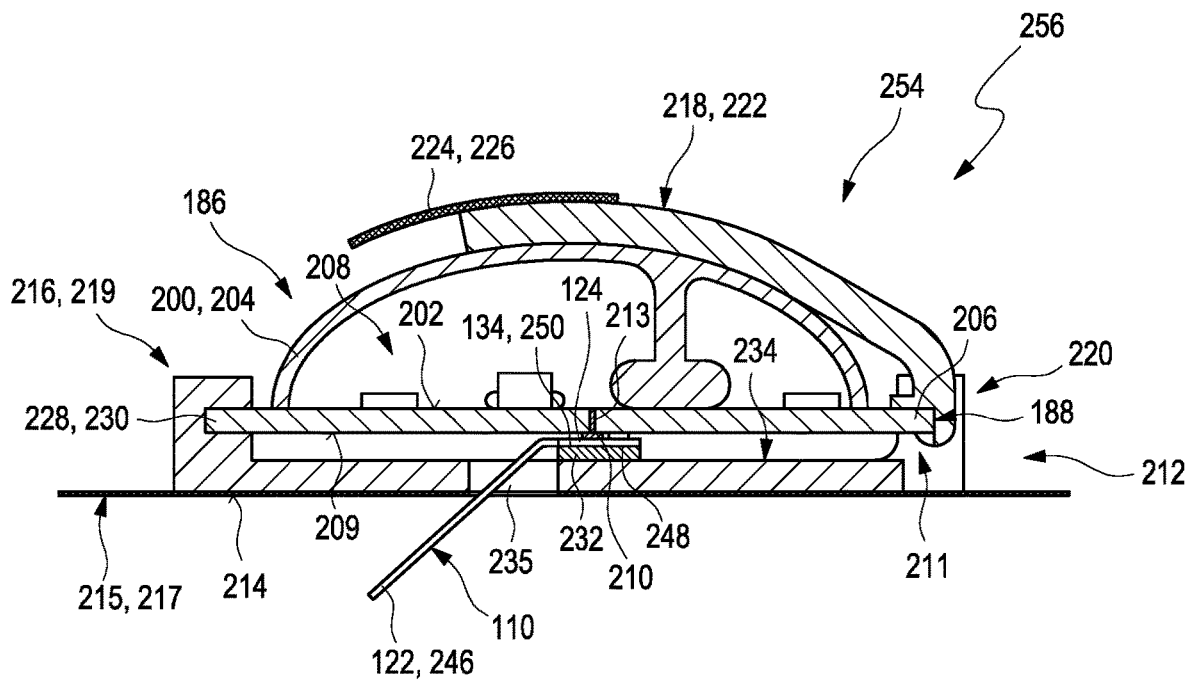
FIGS. 9A to 9B show an exemplary embodiment of a sensor assembly in a cross-sectional view (FIG. 9A) and in a side view (FIG. 9B)
Figure 9:
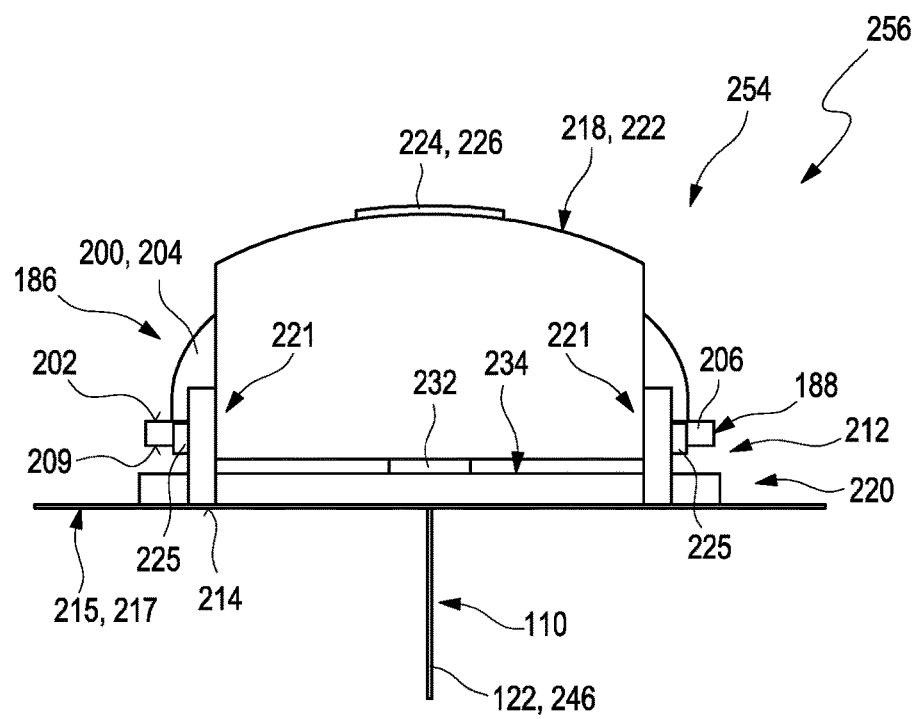
Figure 10:
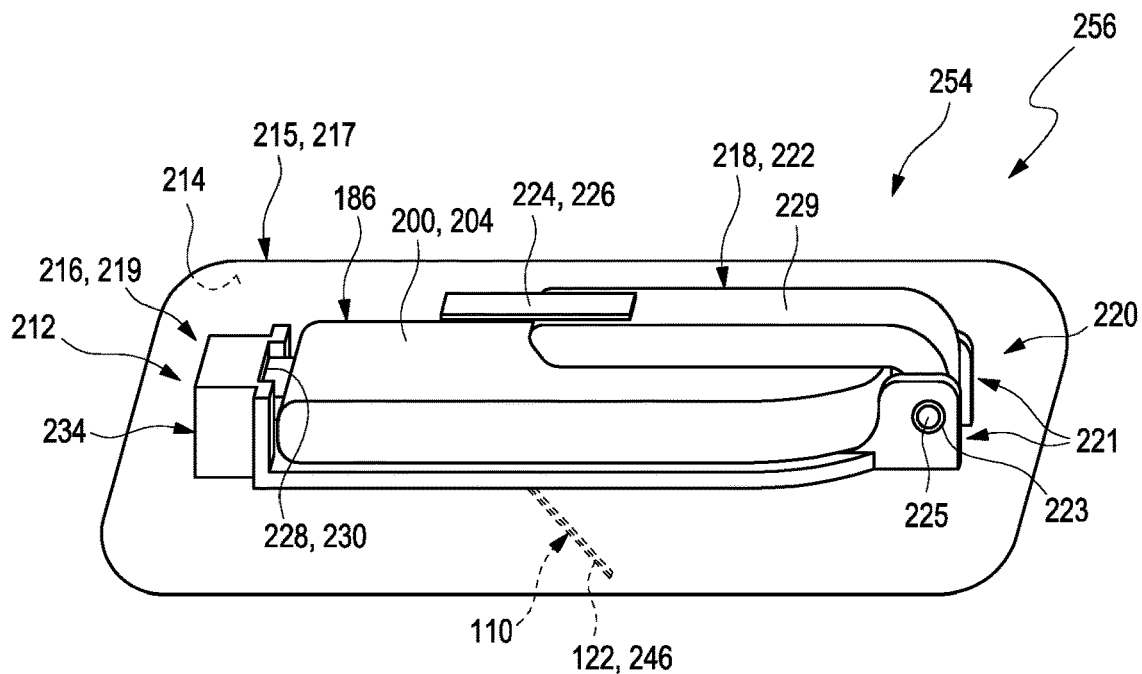
FIGS. 10A to 10B show an exemplary embodiment of a sensor assembly in a perspective view in a fully assembled state (FIG. 10A) and in a disassembled state (FIG. 10B).
Figure 10:
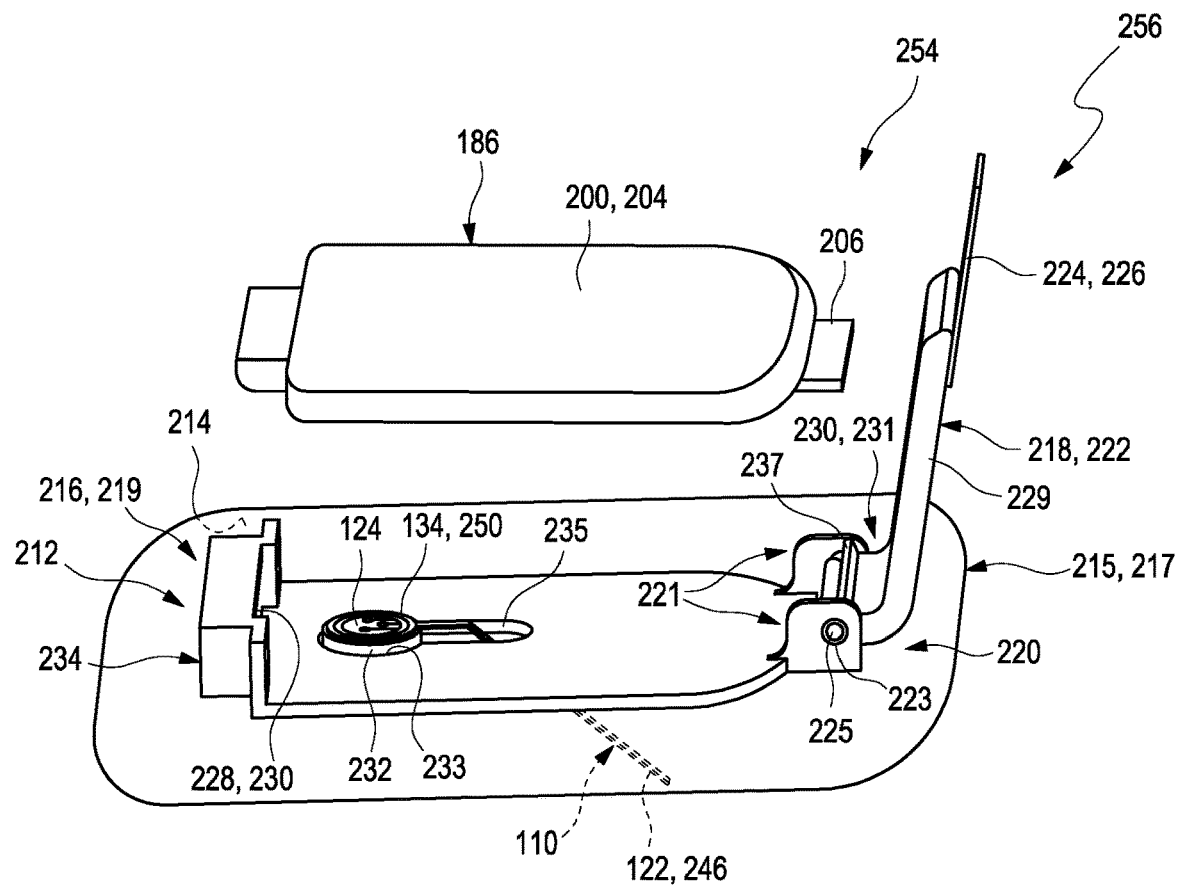

FIGS. 7A to 7C show different embodiments of an insertion element 236. The insertion element 236 may be configured for transferring the sensor 110 as described above to the body mount 212. The insertion element 236 may comprise at least one plunger 238. Further, the insertion element 236 may comprise at least one cannula 242, specifically at least one slotted cannula 244. Thus, the transfer of the sensor 110 to the body mount 212, by using the insertion element 236, may take place simultaneously to an insertion of the shaft 122 of the sensor 110 or a part thereof into the body tissue, even though these processes actually are separate processes and may also be performed independently. Thus, as an example, the insertion element 236 may be designed without the cannula 242, and may be used for connecting the sensor 110 to the body mount 212, only. For implanting or inserting the sensor 110 into the body tissue, a separate tool may be used in this case.

The sensor 110 may be partially, specifically with at least one insertable portion 246, received in the cannula 242. Specifically, the contact portion 124 may be located outside the cannula 242 and the insertable portion 146 may comprise the shaft 122 of the sensor 110 or may be part of the shaft 122.

For adhering the sensor 110 to the body mount 212, one or more first adhesive elements 248 may be used. The at least one first adhesive element 248 may be attached to one or both of the body mount 212 and/or to the sensor 110. The first adhesive element 248, as an example, may comprise at least one adhesive, such as at least one pressure sensitive adhesive, like a polymer adhesive or a silicone-based adhesive. Other examples are feasible. Further, the first adhesive element 248 may also fully or partially be integrated or attached to the pressure element 232. The first adhesive element 248 may be designed to keep the sensor 110 in place, fixedly mounted to the body mount 212, once the sensor 110 is transferred onto the body mount 212 by using the insertion element 236.

Further, for preliminarily attaching the sensor 110 to the insertion element 236, such as to the plunger 238, at least one second adhesive element 250 may be used. The second adhesive element 250 may be attached to and/or integrated into one or both of the sensor 110 and/or the insertion element 236, such as the plunger 238. Specifically, however, the second adhesive element 250 may be attached to or part of the sensor 110. This embodiment specifically may be realized by using the sealing ring 134, which may have adhesive properties, as the second adhesive element 250. Thus, during transfer of the sensor 110 to the body mount 212, the sealing ring 134 may stick to the plunger 238 and, thus, may attach the sensor 110 to a bottom side 252 of the plunger 238.

As can be seen in the figures, the first and second adhesive elements 248, 250 may contact the sensor 110, specifically the contact portion 124 of the sensor 110, on opposite sides thereof. The insertion element 236 may be configured such that the sensor 110 may be inserted into the skin of the user in a direction transverse to a direction of extension of the skin, particularly perpendicular to the direction of extension (FIG. 7B) or in an angle in the range from 20° to 70°, preferably from 30° to 50° (FIGS. 7A and 7C). Other embodiments are feasible.

FIGS. 8A to 8D illustrate a method of mounting the sensor 110 to the body mount 212 attachable to the skin of the user. In a first step, as depicted in FIG. 8A, the body mount 212 may be provided, having the base 234 and the pressure element 232 disposed thereon or integrated therein and with the opening 235 penetrating the base 234. The first adhesive element 248 may be attached to or be part of the pressure element 232. Specifically, this may be realized by using the pressure element 232, which may have adhesive properties, as the first adhesive element 248. The body mount 212, in this state, may be attached to the skin of the user by using the mounting element 217, such as the plaster 215, as disclosed above. The body mount 212 may further comprise the locking mechanism 216 as explained above and as will be disclosed in further detail below.

In a next step, as depicted in FIG. 8B, the sensor 110 and the insertion element 236 as illustrated in FIGS. 7A to 7C may be provided. In a next step, as depicted in FIG. 8C, the sensor 110 may be transferred from an initial position, in which the sensor 110 is attached to the insertion element 236, as depicted in FIG. 8B, into a final position in which the sensor 110 is attached to the body mount 212 via the first adhesive element 248 and released from the insertion element 236, by using the insertion element 236. Thus, during the transfer, the adhesion between the sensor 110 and the body mount 212 may be established by the first adhesive element 248 and the adhesion between the sensor 110 and the insertion element 236, established by the second adhesive element 250 is released. Thereafter, the insertion element 236 may be removed.

In a next step, as depicted in FIG. 8D, the electronics unit 186 may be locked onto the body mount 212 by using the at least one locking mechanism 216 as illustrated in FIGS. 6A to 6C. The electronics unit 186 and the body mount 212 may form a control part 254 of a sensor assembly 256.

In an exemplary embodiment, the plunger 238 was made of Eastar™ Copolyester MN021 natural from Eastman Chemical Company, Kingsport, Tenn., USA by injection molding. Thereby, an injection mold for conducting the injection molding was polished at an area attaching the bottom side 252 of the plunger 238. The base 234 was made of Makrolon® 2458 from Bayer AG, Leverkusen, Germany. The substrate 114 was made of polyimide and was covered with the electrically insulating material 133. The electrically insulating material 133 was made of an solder resist from Dyconex AG, Bassersdorf, Swizerland. The sealing ring 134 was made of Geniomer® 145 from Wacker Chemie AG, Munich, Germany or alternatively of Geniomer® 345 from Wacker Chemie AG, Munich, Germany. The pressure element 232 was made of Geniomer® 345 from Wacker Chemie AG, Munich, Germany. The second adhesive material was made of DURO-TAK 87-4287, Henkel Corporation, Bridgewater, N.J., USA, spray application. Furthermore, the first adhesive element was made of DURO-TAK 387-2051/ 87-2051 from Henkel Corporation, Bridgewater, N.J., USA, spray application.

FIGS. 9A and 9B show an exemplary embodiment of the sensor assembly 256 in a cross-sectional view (FIG. 9A) and in a side view (FIG. 9B). The sensor assembly 256 may comprise the control part 254 having the body mount 212 and the electronics unit 186. For further details, reference can be made to the description of FIGS. 1A to 8D above.

FIGS. 10A and 10B show a further exemplary embodiment of the sensor assembly 256 in a perspective view in a fully assembled state, in which the locking mechanism 216 is locked and in a closed state or closed position (FIG. 10A) and in a disassembled state, in which the locking mechanism 216 is unlocked and in an opened state or opened position (FIG. 10B). As explained above in the context of FIGS. 6A to 6C, this locking or unlocking specifically may be performed by pivoting the lever arm 229 of lever 218.

The sensor assembly 256 may comprise the control part 254 comprising the body mount 212 and the electronics unit 186. Whereas the sensor assembly 256 according to FIGS. 9A and 9B may comprise the electronics unit 186 with an essentially round shape, the sensor assembly 256 may comprise the electronics unit 186 with an essentially flat shape. Thus, however, is simply a design matter, and other embodiments may be feasible. For further details, reference can be made to the descriptions of the FIGS. 1A to 8D.

By mounting the electronics unit 186 onto the body mount 212, the electrical contacts 210 of the electronics unit 186, disposed on the lower side 209 of the electronics unit 186, which in shape and position correspond to the contact pads 118 of the sensor 110, may be pressed onto the contact pads 118 or vice a versa, such that a mutual electrical contact between corresponding contact pads 118 and the electrical contacts 210 may be established. Simultaneously, as symbolically shown in the test setup of FIG. 4C, the sealing ring 134 may be compressed, and a contact region may be isolated from the ambient atmosphere by the sealing ring 134. The pressure element 232 may establish the required deformation of the substrate 114 of the sensor 110 and may provide, in conjunction with the locking mechanism 216, the required pressure for establishing a durable and reliable electrical contact between the sensor 110 and the electronics unit 186.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 sensor
112 intermediate product
114 substrate
116 electrode
118 contact pad
120 electrical trace
122 shaft
124 contact portion
125 surface
126 contact surface area
128 working electrode
130 counter electrode
132 reference electrode
133 electrically insulating material
134 sealing ring
135 insulating surface area
136 insulating layer
138 sealing lip
140 inner perimeter
142 outer perimeter
144 test element
146 first circuit diagram
148 second circuit diagram
150 third circuit diagram
152 end
154 further contact portion
156 counter contact pads
158 ohmmeter
160 voltmeter
162 electrical resistor
164 voltage source
166 micro-ammeter
168 testing setup
170 terminal block
172 clamping screw
174 supporting surface
176 plate
178 first plate
180 second plate
184 force
186 electronics unit
188 base
200 housing
202 upper side
204 watertight housing
206 rim
208 electronics component
209 lower side
210 electrical contacts
211 second guiding structure
212 body mount
213 vias
214 adhesive surface
215 plaster
216 locking mechanism
217 mounting element
218 lever
219 self-locking mechanism
220 end
221 hinge
222 knee lever
223 sleeve
224 flexible extension
225 stud
226 foldable foil 227 protusion
228 receptacle
229 lever arm
230 first guiding structure
231 further receptacle
232 pressure element
233 cavity
234 base
235 opening
236 insertion element
238 plunger
242 cannula
244 slotted cannula
246 insertable portion
248 first adhesive element
250 second adhesive element
252 bottom side
254 control part
256 sensor assembly

What is claimed is:

1. A sensor assembly for detecting at least one analyte in a body fluid, comprising:
   an electrochemical sensor;
   a body mount configured for attachment to a body of a user;
   an inserter configured for transferring the sensor to the body mount;
   a first adhesive configured to attach the sensor to the body mount;
   a second adhesive configured for releasably attaching the sensor to the inserter;
   wherein the sensor assembly is positionable in an initial position in which the sensor is attached to the inserter via the second adhesive and is positionable in a final position in which the sensor is attached to the body mount via the first adhesive;
   wherein transferring the sensor from the initial position to the final position releases the sensor from the inserter; and
   wherein the second adhesive is configured to seal off contacts of the sensor when an electronics unit is attached to the body mount.

2. The sensor assembly according to claim 1, wherein the first adhesive and the second adhesive are configured to contact the sensor on opposing sides.

3. The sensor assembly according to claim 1, wherein the second adhesive is configured to provide a second adhesive force that adheres the sensor to the inserter, wherein the first adhesive is configured to provide a first adhesive force that adheres the sensor to the body mount, wherein the first adhesive force exceeds the second adhesive force.

4. The sensor assembly according to claim 1, wherein one or both of the first adhesive or second adhesive comprise at least one material selected from the group consisting of: a polymer adhesive; a silicone-based adhesive; silicone material; a silicone-based thermoplastic material; a silicone copolymer; an urea copolymer; at least one solvent-based acrylic pressure-sensitive adhesive.

5. The sensor assembly of claim 4, wherein one or both of the first adhesive or second adhesive comprise at least one silicone and/or a silicone polymer.

6. The sensor assembly of claim 4, wherein one or both of the first adhesive or second adhesive comprise a copolymer of dimethylsiloxane and urea.

7. The sensor assembly of claim 4, wherein one or both of the first adhesive or second adhesive comprise at least one solvent-based acrylic material comprising at least one polymer based on acrylic esters.

8. The sensor assembly according to claim 1, wherein the inserter is configured such that a transfer of the sensor from the inserter to the body mount takes place on insertion of a part of the sensor into a body tissue.

9. The sensor assembly according to claim 1, wherein the inserter comprises a plunger, wherein the second adhesive is configured to attach the sensor to the plunger, wherein, in the initial position, the sensor is attached to the plunger via the second adhesive.

10. The sensor assembly according to claim 1, wherein the sensor assembly further comprises a pressure element located between a surface of the body mount and the sensor, wherein the sensor assembly is configured such that the sensor is pressed against the pressure element or vice versa during the transfer of the sensor from the initial position into the final position.

11. The sensor assembly according to claim 10, wherein the pressure element, on at least one surface, comprises one or more cavities configured to act as suction cups.

12. The sensor assembly according to claim 10, wherein one or both of the first adhesive and second adhesive are integrated into the pressure element or attached to the pressure element.

13. The sensor assembly according to claim 1, wherein the inserter is configured such that a surface of the sensor is pressed onto the body mount at an angle of 0° to 10° relative to a skin surface to which the body mount is adhered.

14. The sensor assembly according to claim 1, wherein the inserter is configured such that a surface of the sensor is pressed onto the body mount at an angle of 0° to 6° relative to a skin surface to which the body mount is adhered.

15. The sensor assembly according to claim 1, wherein the sensor assembly further comprises an electronics unit having at least one electronics component for one or more of controlling the detection of the analyte or transmitting measurement data to another component, wherein the electronics unit is reversibly connectable to the body mount.

16. The sensor assembly according to claim 1, wherein the sensor assembly further comprises a removable liner that fully or partially covers the first adhesive, wherein the removable liner is removable for transfer of the sensor into the final position.

17. The sensor assembly according to claim 1, further comprising:
   a substrate;
   at least two electrodes applied to the substrate, the electrodes adapted for detecting the analyte;
   at least two contact pads applied to the substrate;
   at least two electrical traces applied to the substrate, the electrical traces electrically connecting the electrodes and the contact pads; and
   a sealing ring fixedly applied to the substrate, the sealing ring surrounding the contact pads.

18. The sensor assembly according to claim 17, wherein the second adhesive comprises the sealing ring.

19. The sensor assembly of claim 1, wherein the second adhesive comprises a sealing ring.

20. A method of mounting a sensor for detecting at least one analyte in a body fluid to a body mount attachable to a body of a user, comprising:
   providing an electrochemical sensor;
   providing a body mount;

providing an inserter for transferring the sensor to the body mount;

providing a first adhesive attached to one or both of the body mount or the sensor, configured for attaching the sensor to the body mount;

providing a second adhesive attached to one or both of the sensor or the inserter, configured for releasably attaching the sensor to the inserter;

using the inserter to transfer the sensor from an initial position, in which the sensor is attached to the inserter via the second adhesive, into a final position in which the sensor is attached to the body mount via the first adhesive and released from the inserter; and using the second adhesive to seal off contacts of the sensor when an electronics unit is attached to the body mount.

21. The method of claim 20, wherein the second adhesive is provided as a sealing ring.

* * * * *